(12) United States Patent
Kaneko et al.

(10) Patent No.: US 9,637,737 B2
(45) Date of Patent: May 2, 2017

(54) METHOD FOR EVALUATING REDOX ACTIVITY OF NUCLEIC ACID MOLECULE AND NUCLEIC ACID MOLECULE HAVING REDOX ACTIVITY

(75) Inventors: Naoto Kaneko, Tokyo (JP); Katsunori Horii, Tokyo (JP); Jou Akitomi, Tokyo (JP); Shintarou Katou, Tokyo (JP); Iwao Waga, Tokyo (JP)

(73) Assignee: NEC SOLUTION INNOVATORS, LTD., Tokyo (JP)

( * ) Notice: Subject to any disclaimer, the term of this patent is extended or adjusted under 35 U.S.C. 154(b) by 157 days.

(21) Appl. No.: 14/129,392

(22) PCT Filed: Jul. 2, 2012

(86) PCT No.: PCT/JP2012/066912
§ 371 (c)(1),
(2), (4) Date: Jan. 8, 2014

(87) PCT Pub. No.: WO2013/005723
PCT Pub. Date: Jan. 10, 2013

(65) Prior Publication Data
US 2014/0128589 A1    May 8, 2014

(30) Foreign Application Priority Data
Jul. 4, 2011  (JP) ................ 2011-148562

(51) Int. Cl.
| | |
|---|---|
| C12Q 1/68 | (2006.01) |
| C12P 19/34 | (2006.01) |
| C12N 15/113 | (2010.01) |
| C12N 15/115 | (2010.01) |
| C12Q 1/26 | (2006.01) |
| C12N 15/10 | (2006.01) |
| C12N 15/11 | (2006.01) |
| G01N 27/26 | (2006.01) |
| G01N 33/58 | (2006.01) |

(52) U.S. Cl.
CPC ........ *C12N 15/113* (2013.01); *C12N 15/1034* (2013.01); *C12N 15/111* (2013.01); *C12Q 1/26* (2013.01); *C12Q 1/6825* (2013.01); *G01N 27/26* (2013.01); *G01N 33/581* (2013.01); *C12N 15/115* (2013.01); *C12N 2310/127* (2013.01); *C12N 2310/16* (2013.01); *C12N 2310/351* (2013.01); *C12N 2320/10* (2013.01); *C12N 2330/31* (2013.01)

(58) Field of Classification Search
CPC ................ C12Q 1/68; C12N 15/115
See application file for complete search history.

(56) References Cited

U.S. PATENT DOCUMENTS 5,424,186 A   6/1995 Fodor et al.
5,807,522 A   9/1998 Brown et al.

| | | | |
|---|---|---|---|
| 2004/0106190 A1* | 6/2004 | Yang | G01N 33/5438 435/287.2 |
| 2005/0089890 A1* | 4/2005 | Cubicciotti | C07H 21/00 435/6.11 |
| 2007/0092906 A1* | 4/2007 | Murphy | B82Y 30/00 435/6.14 |
| 2010/0000881 A1* | 1/2010 | Franzen | C12Q 1/6825 205/780.5 |
| 2010/0021907 A1 | 1/2010 | Okada et al. | |
| 2011/0033391 A1 | 2/2011 | Weiner et al. | |
| 2014/0165221 A1 | 6/2014 | Weiner et al. | |

FOREIGN PATENT DOCUMENTS

| | | |
|---|---|---|
| CN | 1553188 A | 12/2004 |
| CN | 1885036 A | 12/2006 |
| CN | 100575954 C | 12/2009 |
| CN | 101679473 A | 3/2010 |
| CN | 101965397 A | 2/2011 |
| JP | 10-503841 | 4/1998 |
| JP | 2010-11791 | 1/2010 |
| WO | WO 2005/113813 A2 | 12/2005 |
| WO | WO 2008/073175 A2 | 6/2008 |
| WO | WO 2010/142037 A1 | 12/2010 |

OTHER PUBLICATIONS

Dill et al., Multiplexed analyte and oligonucleotide detection on microarrays using several redox enzymes in conjunction with electrochemical detection. LabChip 6 :1052 (2006).*
Du et al., G-Quadruplex-based DNAzyme for colorimetric detection of cocaine: Using magnetic nanoparticles as the separation and amplification element. Analyst 136 :493 (2011).*
Hintsche et al., Multiplexing of microelectrode arrays in voltammetric measurements. Electroanalysis 12(9) : 660 (2000).*
Katilius et al., Exploring the sequence space of a DNA aptamer using microarrays. Nucleic Acids Research 35 (22) : 7626 (2007).*

(Continued)

*Primary Examiner* — Ethan C Whisenant
(74) *Attorney, Agent, or Firm* — Finnegan, Henderson, Farabow, Garrett & Dunner, L.L.P.

(57) ABSTRACT

The present invention provides a novel technique by which the redox activity of a nucleic acid molecule can be evaluated. An evaluation method of the present invention includes: a detection step of electrochemically detecting a redox reaction to a substrate, the redox reaction being catalyzed by a nucleic acid molecule to be evaluated, using a device that electrochemically detects a redox reaction; and an evaluation step of evaluating redox activity of the nucleic acid molecule from a result of the detection of the redox reaction. As the device, a device in which a base provided with a detection portion is included, the detection portion includes an electrode system, and the nucleic acid molecule to be evaluated is arranged on the base is used. In the present invention, it is preferred that a plurality of kinds of nucleic acid molecule to be evaluated is arranged on the base, and the plurality of kinds of nucleic acid molecules to be evaluated is evaluated by a single device.

22 Claims, 5 Drawing Sheets

(56) References Cited

OTHER PUBLICATIONS

Knight et al., Array-based evolution of DNA aptamers allows modelling of an explicit sequence-fitness landscape. Nucleic Acids Research 37 (1) :e6 (2009).*
Li et al. A Catalytic DNA for porphyrin metallation. Nature Structural Biology 3 (9) :743 (1996).*
Li et al., Recognition of Anionic Porphyrins by DNA Aptamers. Biochemistry 35 :6911 (1996).*
Roth et al., Electrochemical Detection of Short DNA Oligomer Hybridization Using the CombiMatrix ElectraSense Microarray Reader. Electroanalysis 18(19-20) : 1982 (2006).*
Travascio et al., DNA-enhanced peroxidase activity of a DNA aptamer-hemin complex. Chemistry & Biology 5 : 505 (1998).*
White et al., Re-engineering aptamers to support reagentless, self-reporting electrochemical sensors. Analyst 135 : 589 (2010).*
Yao et al., Molecular-beacon-based array for sensitive DNA analysis. Analytical Biochemistry 331 :216 (2004).*
Zhou et al., Mapping peroxidase in plant tissues by scanning electrochemical microscopy. Bioelectrochemistry 54 :151 (2001).*
Office Action issued by the Chinese Patent Office in counterpart Chinese Patent Application No. 201280031760.8 dated Sep. 11, 2015.
B. Baker et al., "An Electronic, Aptamer-Based Small-Molecule Sensor for the Rapid, Label-Free Detection of Cocaine in Adulterated Samples and Biological Fluids", Journal of the American Chemical Society, vol. 128, No. 10, pp. 3138-3139, 2006.
I. Willner et al., "Electronic Aptamer-Based Sensors", Angewandte Chemie International Edition, vol. 46, No. 34, pp. 6408-6418, 2007.
X. Zuo et al., High Specificity, Electrochemical Sandwich Assays Based on Single Aptamer Sequences and Suitable for the Direct Detection of Small-Molecule Targets in Blood and Other Complex Matrices, Journal of the American Chemical Society, vol. 131, No. 20, pp. 6944-6945, 2009.
R. Freeman et al., "Self-assembly of supramolecular aptamer structures for optical or electrochemical sensing", The Analyst, vol. 134, No. 4, pp. 653-656, 2009.
Y. Xiao et al., "A Reagentless Signal-On Architecture for Electronic, Aptamer-Based Sensors via Target-Induced Strand Displacement", Journal of the American Chemical Society, vol. 127, No. 51, pp. 17990-17991, 2005.
Y. Xiao et al., "Electrochemical Detection of Parts-Per-Billion Lead via an Electrode-Bound DNAzyme Assembly", Journal of the American Chemical Society, vol. 129, No. 2, pp. 262-263, 2007.
Partial European Search Report mailed on Jan. 28, 2015 by the European Patent Office in counterpart European Patent Application No. 12807273.3.
Office Action issued by the Chinese Patent Office in counterpart Chinese Patent Application No. 201280031760.8 dated Feb. 16, 2015.
C. Fan et al., "Electrochemical interrogation of conformational changes as a reagentless method for the sequence-specific detection of DNA", PNAS, vol. 100, No. 16, pp. 9134-9137, Aug. 2003.
Y. Mao et al., "Studies of temperature-dependent electronic transduction on DNA hairpin loop sensor", Nucleic Acids Research, vol. 31, No. 18, pp. 1-6, Apr. 2003.

M. Mascini, "Aptamers in Bioanalysis", Chemical Industry Press, pp. 55-94, 2010.
R. K. Hartmann et al., "The Aptamer Handbook—Functional Plogonucleotides and Their Applications", WILEY-VCH, pp. 211-257, 2006.
"Studies on Structural Biology and Modern Pharmacy", Science Press, pp. 96-120, 2008.
"Molecular Mechanisms of Interactions between Antitumor and Antivirus Drugs and Nucleic Acids", Peking University Medical Press, pp. 189-218, 2009.
D. Kong et al., "Structures, Thermal Stability Detection of G-quadruplexes and their Applications in $K^+$ Quantitation", Chemistry Bulletin, pp. 388-395, 2010.
Chinese Office Action issued by the Chinese Patent Office in counterpart Chinese Patent Application No. 201410643532.7, dated Jul. 5, 2016.
C. Teller et al., "Aptamer-DNAzyme Hairpins for Amplified Biosensing", Analytical Chemistry, vol. 81, No. 21, pp. 9114-9119, Nov. 2009.
J. Sambrook et al., Molecular Cloning: A Laboratory Manual $2^{nd}$Ed., Cold Spring Harbor Laboratory Press, 1989 (Northern Hybridization, vol. 1, 7.39 Analysis of Genomic DNA by Southern Hybridization, vol. 2, 9.31).
X. Cheng et al., "General Peroxidase Activity of G-Quadruplex—Hemin Complexes and Its Application in Ligand Screening", Biochemistry, vol. 48, No. 33, pp, 7817-7823, 2009.
G. Pelossof et al., "Amplified Biosensing Using the Horseradish Peroxidase-Mimicking DNAzyme as an Electrocatalyst", Analytical Chemistry, vol. 82, No. 11, pp. 7396-4402, Jun. 2010.
M. Liu et al., "Direct In Vitro Selection of Hemin-Binding DNA Aptamer with Peroxidase Activity", Bull. Chem. Soc. Jpn., vol. 82, No. 1, pp. 99-104, 2009.
M. Liu et al., "Hemin-Binding Aptamers and Aptazymes", American Chemical Society Sym. Ser., vol. 1043, pp. 111-123, 2010.
Q. Guo et al., "Amplified electrochemical DNA sensor using peroxidase-like DNAzyme", Talanta, vol. 83, pp. 500-504, 2010.
Y. Ito, "Design and synthesis of functional polymers by in vitro selection", Polymers for Advanced Technologies, vol. 15, pp. 3-14, 2004.
Y. Ito, "Design and Synthesis of Nano-Devices Using Functional DNAs Obtained by Combinatorial Chemistry", Abstracts, $14^{th}$ conference on combinatorial chemistry, Japan, pp. 108-110, 2002.
A. L. Ghindilis et al., "CombiMatrix oligonucleotide arrays: Genotyping and gene expression assays employing electrochemical detection", Biosensors Bioelectronics, vol. 22, pp. 1853-1860, 2007.
Y. Ito et al., "Immobilization of DNAzyme as a Thermostable Siocatalyst", Biotechnol, Bioeng., vol. 86, pp, 72-77, 2004.
International Search Report mailed Sep. 25, 2012.
Notification of the Second Office Action issued by the State Intellectual Property Office of the People's Republic of China in counterpart Chinese Patent Application No. 201410643532.7, dated Jan. 11, 2017.
Han et al., "G-quadruplex DNA: a potential target for anti-cancer drug design", TiPS, 2000, vol. 21, pp. 136-142, (2000).
Jing et al., "Structure-Activity of Tetrad-forming Oligonucleotides as a Potent Anti-HIV Therapeutic Drug", The Journal of Biological Chemistry, the American Society for Biochemistry and Molecular Biology Inc., vol. 273, No. 52, Issue of Dec. 25, pp. 34992-34999, (1998).

* cited by examiner

METHOD FOR EVALUATING REDOX ACTIVITY OF NUCLEIC ACID MOLECULE AND NUCLEIC ACID MOLECULE HAVING REDOX ACTIVITY

TECHNICAL FIELD

The present invention relates to a method for evaluating redox activity of a nucleic acid molecule and a nucleic acid molecule having redox activity.

BACKGROUND ART

It is required to detect a target in various fields such as clinical medical care, food, and environment. In the detection of a target, interactions with the target are generally utilized, and among them, a method using an antibody that specifically binds to a target is widely used. In this method, for example, a target is bound to an antibody labeled with oxidoreductase such as peroxidase. Then, a chromogenic reaction is conducted by the enzyme in the labeled antibody using a chromogenic substrate, and the development in color is detected. By the detection of the development in color, analyses of the target such as qualitative analysis and quantitative analysis are performed indirectly.

However, since the antibody is obtained by immunizing animals, it is really difficult to obtain an antigen specific to a toxic target or a low-molecular-weight target. Hence, recently, a nucleic acid that binds to a target, i.e., a nucleic acid aptamer (hereinafter, merely referred to as an aptamer) has been focused on. The aptamer can be obtained in a test tube. Therefore, for example, it is possible to obtain aptamers to a toxic target and a low-molecular-weight target. Further, it has been attempted to use such aptamer as substitute for the antibody in detection of a target in combination with DNAzyme exerting catalytic activity as in peroxidase. The DNAzyme generally is DNA that exerts a catalytic property of peroxidase by having a guanine-rich structural motif, having a G-quadruplex structure, and forming a complex by binding to hemin.

In the detection of a target, a single-stranded nucleic acid element obtained by linking a single-stranded aptamer and a single-stranded DNAzyme is specifically utilized (Non-Patent Document 1). The single-stranded nucleic acid element forms a stem structure by self-annealing in the absence of a target, and the DNAzyme cannot form G-quadruplex by the stem structure. Therefore, the DNAzyme in the single-stranded nucleic acid element cannot bind to hemin and cannot achieve a catalytic property in the absence of a target. On the other hand, in the presence of a target, the single-stranded nucleic acid element releases the stem structure by binding the target to the aptamer. Therefore, in the presence of a target, the DNAzyme in the single-stranded nucleic acid element forms G-quadruplex and exerts the catalytic property by binding to hemin. Thus, when a chromogenic substrate to redox activity is present together, a chromogenic reaction occurs in the presence of the target, and a chromogenic reaction does not occur in the absence of the target. Therefore, it becomes possible to analyze the target by detecting the chromogenic reaction. Furthermore, it is not required to label the target, and thus, it becomes possible to directly detect various targets including a low-molecular-weight target.

As described above, the single-stranded nucleic acid element is required to control activity of the DNAzyme by a conformation of the aptamer. Therefore, for example, it is desired to combine DNAzyme whose activity can be easily controlled according to the sequence of an aptamer to be used.

However, there is only a limited number of DNAzymes that have been reported. Therefore, when a combination with a predetermined aptamer is decided, there has no choice but to select from the limited number of DNAzymes. Thus, there is a limitation in structuring a nucleic acid element with superior accuracy according to the target. Moreover, in order to make it possible to perform detection with superior sensitivity, DNAzyme which highly exerts redox activity is required.

Therefore, it has been attempted to obtain novel DNAzyme. However, in screening of DNAzyme, there has no choice but to determine each of activities of candidate nucleic acid molecules, and the operation thereof is really complicated.

PRIOR ART DOCUMENT

Non-Patent Document

Non-Patent Document 1: Teller et al., Anal. Chem., 2009, vol. 81, p. 9114-9119

SUMMARY OF INVENTION

Problem to be Solved by the Invention

Hence, the present invention is intended to provide a novel technique by which redox activity of a nucleic acid molecule can be easily evaluated.

Means for Solving Problem

The evaluation method according to the present invention is a method for evaluating redox activity of a nucleic acid molecule, the method including: a detection step of electrochemically detecting a redox reaction to a substrate, the redox reaction being catalyzed by at least one nucleic acid molecule to be evaluated, using a device that electrochemically detects a redox reaction; and an evaluation step of evaluating redox activity of the at least one nucleic acid molecule from a result of the detection of the redox reaction, wherein the device includes a base provided with a detection portion, the detection portion includes an electrode system, and the nucleic acid molecule to be evaluated is arranged on the base.

The nucleic acid molecule according to the present invention is a nucleic acid molecule having redox activity, containing at least one polynucleotide selected from the group consisting of SEQ ID NOs: 1 to 132.

Effects of the Invention

According to the evaluation method of the present invention, the presence or absence of redox activity of a nucleic acid molecule to be evaluated and the intensity of the redox activity can be evaluated easily. Moreover, according to the evaluation method of the present invention, a plurality of kinds of nucleic acid molecules can be evaluated simultaneously, for example. Therefore, an intended nucleic acid molecule can be effectively screened. The nucleic acid molecule having redox activity is, for example, as mentioned above, used as substitute for an enzyme such as peroxidase and thus is useful in various fields such as clinical medical care, food, and environment.

BRIEF DESCRIPTION OF DRAWINGS

FIG. 1A shows results in the case of pH7.4. FIG. 1B shows results in the case of pH8.0. FIG. 1C shows results in the case of pH8.5. FIG. 1D shows results in the case of pH9.0.

FIG. 2A is a graph showing reproducibility in a first-time electrical signal measurement and a second-time electrical signal measurement by the same microarray. FIG. 2B is a graph showing reproducibility in DNAzymes having the same length of a spacer.

FIG. 4A is a graph showing reproducibility in a first-time electrical signal measurement and a second-time electrical signal measurement by the same microarray. FIG. 4B is a graph showing reproducibility in the second-time electrical signal measurement and a third-time electrical signal measurement by the same microarray. FIG. 4C is a graph showing reproducibility in the first-time electrical signal measurement and the third-time electrical signal measurement by the same microarray.

FIG. 5A shows a result in the case of c-Myc. FIG. 5B shows a result in the case of SA. FIG. 5C shows a result in the case of EAD2. FIG. 5D shows a result in the case of TA.

DESCRIPTION OF EMBODIMENTS

1. Evaluation Method

Figure 1A:
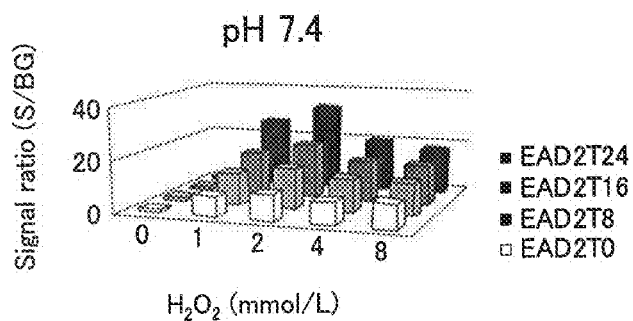
FIGS. 1A to 1D are graphs showing electrical signals of DNAzyme under different conditions of pH, the length of a spacer on an electrode, and the concentration of hydrogen peroxide in Example 1 of the present invention.

The evaluation method according to the present invention is, as mentioned above, a method for evaluating redox activity of a nucleic acid molecule, the method including: a detection step of electrochemically detecting a redox reaction to a substrate, the redox reaction being catalyzed by at least one nucleic acid molecule to be evaluated, using a device that electrochemically detects a redox reaction; and an evaluation step of evaluating redox activity of the at least one nucleic acid molecule from a result of the detection of the redox reaction, wherein the device includes a base provided with a detection portion, the detection portion includes an electrode system, and the nucleic acid molecule to be evaluated is arranged on the base.

Only one kind of the nucleic acid molecule to be evaluated may be used, and it is preferred that the nucleic acid molecule to be evaluated includes a plurality of kinds of nucleic acid molecules, for example. In the latter case, for example, by arranging a plurality of kinds of nucleic acid molecules on the base, the plurality of kinds of nucleic acid molecules can be evaluated using the single base.

The nucleic acid molecule to be evaluated is, for example, a molecule containing a nucleotide residue. The nucleic acid molecule may be, for example, a molecule composed of only a nucleotide residue or a molecule containing a nucleotide residue. Examples of the nucleotide include ribonucleotide, deoxyribonucleotide, and derivatives thereof. The nucleic acid molecule may contain any one kind of, two or more kinds of, or all of ribonucleotide, deoxyribonucleotide, and derivatives thereof. Specifically, the nucleic acid molecule may be, for example, RNA containing ribonucleotide and/or a derivative thereof, DNA containing deoxyribonucleotide and/or a derivative thereof, or a chimera (DNA/RNA) containing the former and the latter. The nucleic acid molecule may be a single strand or a double strand and is preferably a single strand. When the nucleic acid molecule is a single strand, examples of the nucleic acid molecule include a single-stranded DNA, a single-stranded RNA, and a single-stranded chimera (DNA/RNA). When the nucleic acid molecule is a double strand, examples of the nucleic acid molecule include a double-stranded DNA, a double-stranded RNA, a DNA-RNA double strand, and a double-stranded chimera (DNA/RNA). The length of the nucleic acid molecule is not particularly limited and is, for example, from 11 to 80 bases.

The nucleotide may include, as bases, for example, natural bases (non-artificial bases) and non-natural bases (artificial bases). Examples of the natural bases include A, C, G, T, U, and modified bases thereof. Examples of the modification include methylation, fluorination, amination, and thiation. Examples of the non-natural bases include 2'-fluoropyrimidine and 2'-O-methylpyrimidine, and specific examples thereof include 2'-fluorouracil, 2'-aminouracil, 2'-O-methyluracil, and 2-thiouracil. The nucleotide may be, for example, modified nucleotide, and examples of the modified nucleotide include a 2'-methylated-uracil nucleotide residue, a 2'-methylated-cytosine nucleotide residue, a 2'-fluorinated-uracil nucleotide residue, a 2'-fluorinated-cytosine nucleotide residue, a 2'-aminated-uracil nucleotide residue, a 2'-aminated-cytosine nucleotide residue, a 2'-thiated-uracil nucleotide residue, and a 2'-thiated-cytosine nucleotide residue. Examples of the nucleic acid molecule include PNA (peptide nucleic acid) and LNA (Locked Nucleic Acid).

In the present invention, the redox reaction is only necessary to be a reaction in which a transfer of electrons between two substrates is generated in a process of generating a product from the substrates, for example. The kind of the redox reaction is not particularly limited. The activity that catalyzes the redox reaction can be, for example, activity that is the same as an enzyme, and can be, specifically, for example, activity that is the same as peroxidase (hereinafter also referred to as peroxidase-like activity). The peroxidase-like activity can be, for example, horseradish-derived peroxidase (HRP) activity. When the nucleic acid molecule to be evaluated is DNA and has the redox activity, the DNA can be referred to as DNA enzyme or DNAzyme, for example. When the nucleic acid molecule is RNA and has the redox activity, the RNA can be referred to as RNA enzyme or RNAzyme, for example.

In the present invention, the detection portion of the device is only necessary to detect an electrical signal that is generated by a redox reaction that is catalyzed by the nucleic acid molecule to be evaluated. The detection portion includes an electrode system as mentioned above. The electrode system may include a working electrode and a counter electrode or may include a working electrode, a counter electrode, and a reference electrode, for example.

The material of each electrode is not particularly limited, and examples thereof include platinum, silver, gold, and carbon. Examples of the working electrode and the counter electrode include a platinum electrode, a silver electrode, a gold electrode, and a carbon electrode. The reference electrode can be, for example, a silver/silver chloride electrode. The silver/silver chloride electrode can be formed by laminating a silver chloride electrode on a silver electrode, for example.

The detection portion can be formed by arranging the electrodes on the surface of the base, for example. A method for arranging the electrodes is not particularly limited, and a conventionally known method can be employed, for example. Specific examples of the method include thin-film forming methods such as an evaporation method, a sputtering method, a screen printing method, and a plating method. The electrodes may be arranged directly or indirectly on the base, for example. The indirect arrangement can be, for example, an arrangement via other members.

The base is not particularly limited and is, for example, preferably a base having an insulating surface. The base may be, for example, a base containing an insulating material or being composed of an insulating material or a base including an insulating layer that has a surface containing an insulating material or an insulating layer composed of the insulating material. The insulating material is not particularly limited, and examples thereof include conventionally known materials such as glass, ceramics, insulating plastics, and paper. The insulating plastic is not particularly limited, and examples thereof include a silicone resin, a polyimide resin, an epoxy resin, and a fluorine resin.

As mentioned above, only one kind of the nucleic acid molecule to be evaluated may be used, it is preferred that the nucleic acid molecule to be evaluated includes a plurality of kinds of nucleic acid molecules, and specifically, the plurality of kinds of nucleic acid molecules is arranged on the base. The device is, for example, preferably a microarray obtained by arranging the plurality of nucleic acid molecules on the base. It is preferred that the plurality of kinds of nucleic acid molecules is arranged on the base in the matrix state, for example. In order to make it possible to detect a redox reaction of the nucleic acid molecule according to the kind thereof, it is preferred that the device has a plurality of detection portions, and a different kind of nucleic acid molecule is arranged in each detection portion, for example. Specifically, the device can be formed by fractionating the surface of the base into matrixes, forming an electrode system such as mentioned above in each fractional region to form detection portions, and arranging the nucleic acid molecule in each detection portion, for example. Moreover, a device obtained by binding the nucleic acid molecule to be evaluated to a probe on a commercially available electrochemical detection-type system microarray can be used as a device for evaluation. The commercially available microarray can be, for example, CombiMatrix ElectraSense microarray (trade name) (manufactured by CombiMatrix).

The nucleic acid molecule to be evaluated is only necessary to be arranged on the base as mentioned above and is preferably immobilized on the base. The nucleic acid molecule may be arranged directly or indirectly on the base, for example. Specifically, the nucleic acid molecule is, for example, preferably arranged on the detection portion in the base, more preferably arranged on any of the electrodes in the detection portion, and yet more preferably arranged on the working electrode among the electrodes. The nucleic acid molecule may be arranged directly or indirectly on the detection portion or any of the electrodes, for example.

Hereinafter, "arrangement or immobilization of the nucleic acid molecule on the base" encompasses the meaning of arrangement or immobilization on the detection portion in the base or any of the electrodes in the detection portion, unless otherwise shown.

A method for arranging the nucleic acid molecule is not particularly limited, and a known nucleic acid immobilization method can be employed. The above-described immobilization method can be, for example, a method for immobilizing a previously provided nucleic acid molecule on the base, preferably on the detection portion, more preferably on any of the electrodes. This method is, for example, a method utilizing photolithography, and a specific example thereof is shown in U.S. Pat. No. 5,424,186 or the like. Furthermore, the immobilization method can be, for example, a method for synthesizing a nucleic acid on the base, preferably on the detection portion, more preferably on any of the electrodes. This method can be, for example, a spot method, and a specific example thereof is shown in U.S. Pat. No. 5,807,522, JP H10-503841, or the like.

The nucleic acid molecule may be immobilized or the base in any of the 5' end side and the 3' end side.

The nucleic acid molecule is preferably arranged on the base via a linker, for example. The linker preferably contains a nucleotide residue, for example. The linker may be composed of only a nucleotide residue or may contain a nucleotide residue, for example. The nucleotide is the same as mentioned above. The length of the linker is not particularly limited and is, for example, from 1 to 60 bases, preferably from 6 to 60 bases, more preferably from 20 to 30 bases. The linker is also referred to as a spacer, for example.

In the device, the nucleic acid molecule to be evaluated may be in the state of linking with an aptamer, for example. Hereinafter, an object obtained by linking between the nucleic acid molecule to be evaluated and the aptamer is referred to as a nucleic acid element. The aptamer is not particularly limited and is, for example, an aptamer capable of binding to a specific target. For example, it is preferred that the aptamer is a nucleic acid molecule containing a nucleotide residue as a component. The nucleotide is not particularly limited and is the same as mentioned above. For example, the aptamer capable of binding to the target can be produced by a conventionally known SELEX (Systematic Evolution of Ligands by Exponential Enrichment) method or the like. The aptamer may be, for example, a single strand or a double strand and is preferably a single strand.

The nucleic acid molecule and the aptamer may be, for example, directly or indirectly bound to each other. In the latter case, they may be bound to each other via a linker, for example. For example, the 5' end of one of the nucleic acid molecule and the aptamer may be linked with the 3' end of the other, the 5' end of the nucleic acid molecule may be linked with the 5' end of the aptamer, or the 3' end of the nucleic acid molecule may be linked with the 3' end of the aptamer.

When the aptamer is linked with the nucleic acid molecule, it is preferred that one end of the nucleic acid molecule is bound to the base, and the other end is bound to the aptamer, for example. As mentioned above, the base can be bound to the nucleic acid molecule via a linker, and the nucleic acid molecule can be bound to the aptamer via a linker, for example. It is preferred that the linkage between the nucleic acid molecule and the aptamer is, for example, a linkage between a single stranded nucleic acid molecule and a single-stranded aptamer. The nucleic acid element obtained by linking between the nucleic acid molecule and the aptamer may form a stem structure and/or a loop structure by self-annealing, for example.

With respect to the evaluation method according to the present invention, a first embodiment shows, as an example, a method using a device in which the nucleic acid molecule to be evaluated is arranged, and a second embodiment shows, as an example, a method using a device in which the nucleic acid molecule binding to the aptamer is arranged, i.e., a device in which the nucleic acid element is arranged. The present invention is not limited to these embodiments.

First Embodiment

In the first embodiment of the present invention, a device in which a nucleic acid molecule to be evaluated is arranged on the base is used as mentioned above.

First, in the detection step, for example, a redox reaction catalyzed by a nucleic acid molecule is electrochemically detected in the presence of a substrate. When the nucleic acid molecule has redox activity, a product is generated from the substrate by the nucleic acid molecule, for example, and in the process of the generation, electrons are transferred, for example. This electron transfer can be electrochemically detected as an electrical signal in a detection portion of the device by applying a voltage to electrodes, for example. The detection of the electrical signal can be performed by measuring intensity of the electrical signal such as a current, for example.

The substrate can be externally supplied to the nucleic acid molecule in the device in the detection step, for example.

The substrate is not particularly limited, and examples thereof include hydrogen peroxide, 3,3',5,5'-Tetramethylbenzidine (TMB), 1,2-Phenylenediamine (OPD), 2,2'-Azinobis(3-ethylbenzothiazoline-6-sulfonic Acid Ammonium Salt (ABTS), 3,3'-Diaminobenzidine (DAB), 3,3'-Diaminobenzidine Tetrahydrochloride Hydrate (DAB4HCl), 3-Amino-9-ethylcarbazole (AEC), 4-Chloro-1-naphthol (4ClN), 2,4,6-Tribromo-3-hydroxybenzoic Acid, 2,4-Dichlorophenol, 4-Aminoantipyrine, 4-Aminoantipyrine Hydrochloride, and luminol.

In the detection step, porphyrin can be present together besides the substrate, for example. Some of known DNAzymes exert superior redox activity by forming a complex with porphyrin, for example. Thus, in the present invention, for example, porphyrin may be caused to be present together to form a complex with the porphyrin and detect redox activity of the complex.

The porphyrin is not particularly limited, and examples thereof include unsubstituted porphyrin and a derivative thereof. The derivative can be, for example, metal porphyrin obtained by forming a complex of substituted porphyrin and a metal element. The substituted porphyrin can be, for example, N-methylmesoporphyrin. The metal porphyrin can be, for example, hemin that is a ferric($Fe^{3+}$) complex. The porphyrin is, for example, preferably the metal porphyrin, more preferably hemin.

In the detection step, conditions under which the redox reaction is performed are not particularly limited. The pH is, for example, from 7.4 to 9.0, preferably from 7.4 to 8.5, more preferably 7.4. It is preferred that the pH is adjusted using a buffer solution, for example, and a buffer solution such as Tris-HCl having the above-mentioned pH can be used, for example. The substrate is preferably added to the nucleic acid molecule as a substrate solution by mixing with a buffer solution, for example. The concentration of the substrate in the substrate solution is not particularly limited and is, for example, from 10 to 200 mmol/L, preferably from 20 to 100 mmol/L, more preferably from 40 to 60 mmol/L, particularly preferably 50 mmol/L.

Then, based on a result of the detection in the detection step, redox activity of the nucleic acid molecule is evaluated in an evaluation step. In the evaluation step, the presence or absence of redox activity or the intensity of the redox activity may be evaluated, for example. In the latter case, for example, relative intensity of the activity can be evaluated relative to redox activity of any nucleic acid molecule, and the any nucleic acid molecule preferably has redox activity.

Second Embodiment

In the second embodiment of the present invention, as mentioned above, a device in which a nucleic acid molecule to be evaluated bound to an aptamer is arranged on a base is used. The second embodiment is the same as the first embodiment unless otherwise indicated.

First, in the detection step, for example, a redox reaction catalyzed by a nucleic acid molecule is electrochemically detected in the presence of a substrate and a target. It is particularly preferred that the detection step includes a step of detecting a redox reaction in the presence of the substrate and the in the absence of the target and a step of detecting a redox reaction in the presence of the substrate and the target. Any of the detection in the absence of a target and the detection in the presence of a target may be performed prior to the other. For example, it is preferred that the detection in the absence of a target is performed prior to the other because the target binding to an aptamer is not required to be released.

The reason why the detection in the absence of a target and the detection in the presence of a target are performed is as follows. In the case where an aptamer capable of binding to a target and a nucleic acid molecule having redox activity are used in detection of a target, it is desired that the nucleic acid molecule having redox activity exerts activity only when the target is present and does not exert activity when the target is absent. This is because, when activity is exerted in the absence of a target, a false-positive result is obtained in the detection of the target. Therefore, the presence or absence of redox activity in the absence of a target and the presence or absence of redox activity in the presence of a target are important for establishing an electrochemical method in the detection of a target using an aptamer.

It is considered that the following structural relationship is satisfied between the nucleic acid molecule and the aptamer in the case where the nucleic acid molecule does not exert activity in the absence of a target and exerts activity in the presence of a target, for example. The aptamer generally changes its conformation by recognizing and binding to a target. Therefore, by a conformation of an aptamer in the absence of a target, the nucleic acid molecule binding to the aptamer has a structure in which activity is switched off. On the other hand, by a conformation of the aptamer changed by binding to the target, suppression of activity of the nucleic acid molecule is released, so that the activity of the nucleic acid molecule is switched on only in the case where a target is present.

In the detection step, the substrate and the target can be externally supplied to the nucleic acid molecule in the device, for example. The order of adding the substrate and the target is not particularly limited. For example, it is possible that one of them is added, and the other is thereafter added, or both of them are added at the same time. Moreover, the porphyrin may be present together as in the first embodiment.

The substrate is not particularly limited and is the same as mentioned above. The target and the aptamer are not particularly limited, and a desired target and an aptamer capable of binding thereto can be used.

Then, in the evaluation step, based on a result of the detection in the detection step, redox activity of the nucleic acid molecule is evaluated. In the evaluation step, the presence or absence of redox activity or the intensity of the redox activity may be evaluated, for example. In the latter case, for example, relative intensity of the activity can be evaluated relative to redox activity of any nucleic acid molecule, and the any nucleic acid molecule preferably has redox activity.

It is preferred that in the evaluation step, redox activity of a nucleic acid molecule that does not exert redox activity in the absence of a target is evaluated in the presence of a target, for example. In the evaluation step, the presence or absence of redox activity or the intensity of redox activity may be evaluated, for example. In the latter case, for example, relative intensity of the activity can be evaluated relative to redox activity of any nucleic acid molecule.

2. Screening Method

The screening method according to the present invention is, as mentioned above, a method for screening a nucleic acid molecule having redox activity, including: evaluating redox activity of at least one nucleic acid molecule to be evaluated by the method according to the present invention using a device; and screening a nucleic acid molecule having redox activity.

The screening method according to the present invention is characterized in that redox activity of the nucleic acid molecule to be evaluated is evaluated by the evaluation method according to the present invention, and other steps and conditions are not at all limited.

In the present invention, based on a result of the evaluation of redox activity, a nucleic acid molecule exerting redox activity can be selected, and furthermore, a nucleic acid molecule exerting relatively intense redox activity can be selected as an intended nucleic acid molecule, for example. Moreover, as mentioned above, for example, a nucleic acid molecule that does not exert activity in the absence of a target and exerts activity in the presence of a target can be selected as an intended nucleic acid molecule.

3. Nucleic Acid Molecule having Redox Activity

The nucleic acid molecule having redox activity according to the present invention contains at least one polynucleotide selected from the group consisting of the following (a) to (d):

(a) a polynucleotide composed of any of base sequences of SEQ ID NOs: 1 to 132;

(b) a polynucleotide being composed of a base sequence obtained by deletion, substitution, insertion and/or addition of one or more bases in any of the base sequences in the polynucleotide (a) and having redox activity;

(c) a polynucleotide being composed of a base sequence having an identity of 80% or more to any of the base sequences in the polynucleotide (a) and having redox activity; and (d) a polynucleotide being composed of a base sequence complementary to a polynucleotide that can hybridize with the polynucleotide (a) under stringent conditions and having redox activity.

The nucleic acid molecule according to the present invention may be, for example, a molecule being composed of or containing any of the polynucleotides (a) to (d). In the latter case, the nucleic acid molecule according to the present invention may contain two or more of the polynucleotides (a) to (d) as described below, for example. The two or more of the polynucleotides may be the same sequences or different sequences. In the latter case, the nucleic acid molecule according to the present invention may further have a linker and/or an additional sequence, for example. The nucleic acid molecule according to the present invention is also referred to as DNAzyme.

The polynucleotide (a) is a polynucleotide composed of any of base sequences of SEQ ID NOs: 1 to 132.

TABLE 1

| SEQ ID NO: | Name | Sequence |
|---|---|---|
| 1 | c0984 | TGAGGGCCGGGTGGGTCGGGAA |
| 2 | c0568 | TGAGGGGAGGGCGGGTCGGGAA |
| 3 | c0067 | TGAGGGATGGGAGGGAGGGGAA |
| 4 | c0192 | TGAGGGAGGGCGGGCCGGGAA |
| 5 | c0524 | TGAGGGGAGGGAGGGGCGGGAA |
| 6 | c0451 | TGAGGGTCGGGAGGGAGGGGAA |
| 7 | c0541 | TGAGGGGAGGGTGGGCAGGGAA |
| 8 | c0629 | TGAGGGGTGGGCGGGTAGGGAA |
| 9 | c0184 | TGAGGGAGGGCGGGTCGGGAA |
| 10 | c0760 | TGAGGGGCGGGCGGGTCGGGAA |
| 11 | c0728 | TGAGGGGCGGGTGGGTCGGGAA |
| 12 | e0064 | CTGGGCGGGCGGGCGGGA |
| 13 | c0719 | TGAGGGGCGGGAGGGCGGGGAA |
| 14 | c0531 | TGAGGGGAGGGTGGGAGGGGAA |
| 15 | c0711 | TGAGGGGCGGGAGGGTGGGGAA |
| 16 | c0096 | TGAGGGATGGGTGGGCCGGGAA |
| 17 | c0595 | TGAGGGGTGGGTGGGAGGGGAA |
| 18 | c0335 | TGAGGGTTGGGAGGGCGGGGAA |
| 19 | c0456 | TGAGGGTCGGGAGGGTCGGGAA |
| 20 | c0756 | TGAGGGGCGGGCGGGACGGGAA |
| 21 | c0717 | TGAGGGGCGGGAGGGCAGGGAA |
| 22 | c0712 | TGAGGGGCGGGAGGGTCGGGAA |
| 23 | c0562 | TGAGGGGAGGGCGGGATGGGAA |
| 24 | c0713 | TGAGGGGCGGGAGGGGAGGGAA |
| 25 | c0735 | TGAGGGGCGGGTGGGCGGGGAA |
| 26 | e0021 | CTGGGTGGGTGGGAGGGA |
| 27 | c0607 | TGAGGGTGGGTGGGCGGGGAA |

TABLE 1-continued

| SEQ ID NO: | Name | Sequence |
|---|---|---|
| 28 | c0722 | TGAGGGGCGGGTGGGATGGGAA |
| 29 | c0600 | TGAGGGGTGGGTGGGTCGGGAA |
| 30 | e0032 | CTGGGTGGGCGGGCGGGA |
| 31 | c0544 | TGAGGGGAGGGTGGGCCGGGAA |
| 32 | c0455 | TGAGGGTCGGGAGGGTGGGAA |
| 33 | c0605 | TGAGGGGTGGGTGGGCAGGGAA |
| 34 | c0718 | TGAGGGGCGGGAGGGCTGGGAA |
| 35 | c0586 | TGAGGGGTGGGAGGGGTGGGAA |
| 36 | c0344 | TGAGGGTTGGGTGGGTCGGGAA |
| 37 | c0152 | TGAGGGAGGGTGGGTCGGGAA |
| 38 | c0630 | TGAGGGGTGGGCGGGTTGGGAA |
| 39 | c0632 | TGAGGGGTGGGCGGGTCGGGAA |
| 40 | c0626 | TGAGGGGTGGGCGGGATGGGAA |

TABLE 2

| SEQ ID NO: | Name | Sequence |
|---|---|---|
| 41 | c0762 | TGAGGGGCGGGCGGGGTGGGAA |
| 42 | c0707 | TGAGGGGCGGGAGGGAGGGGAA |
| 43 | c0750 | TGAGGGGCGGGCGGGTGGGAA |
| 44 | c0543 | TGAGGGGAGGGTGGGCGGGGAA |
| 45 | c0637 | TGAGGGGTGGGCGGGCAGGGAA |
| 46 | c0606 | TGAGGGGTGGGTGGGCTGGGAA |
| 47 | c0895 | TGAGGGCTGGGCGGGCGGGAA |
| 48 | c0753 | TGAGGGGCGGGCGGGAAGGGAA |
| 49 | c0625 | TGAGGGGTGGGCGGGAAGGGAA |
| 50 | c0584 | TGAGGGGTGGGAGGGTCGGGAA |
| 51 | c0567 | TGAGGGGAGGGCGGGTGGGAA |
| 52 | c0599 | TGAGGGGTGGGTGGGTGGGAA |
| 53 | c0520 | TGAGGGGAGGGAGGGTCGGGAA |
| 54 | c0636 | TGAGGGGTGGGCGGGCGGGAA |
| 55 | c0627 | TGAGGGGTGGGCGGGAGGGAA |
| 56 | c0519 | TGAGGGGAGGGAGGGTGGGAA |
| 57 | c0343 | TGAGGGTTGGGTGGGTGGGAA |
| 58 | c0628 | TGAGGGGTGGGCGGGACGGGAA |
| 59 | c0383 | TGAGGGTTGGGCGGGCGGGAA |
| 60 | c0856 | TGAGGGCTGGGTGGGTCGGGAA |
| 61 | c0709 | TGAGGGGCGGGAGGGTAGGGAA |
| 62 | c0574 | TGAGGGGAGGGCGGGCTGGGAA |
| 63 | c0842 | TGAGGGCTGGGAGGGGTGGGAA |

TABLE 2-continued

| SEQ ID NO: | Name | Sequence |
|---|---|---|
| 64 | c0638 | TGAGGGGTGGGCGGGCTGGGAA |
| 65 | c0583 | TGAGGGGTGGGAGGGTGGGAA |
| 66 | c0472 | TGAGGGTCGGGTGGGTCGGGAA |
| 67 | c0463 | TGAGGGTCGGGAGGGCGGGAA |
| 68 | e0018 | CTGGGTGGGAGGGTGGGA |
| 69 | c0736 | TGAGGGGCGGGTGGGCCGGGAA |
| 70 | c0604 | TGAGGGGTGGGTGGGCGGGAA |
| 71 | c0591 | TGAGGGGTGGGAGGGCGGGAA |
| 72 | c0792 | TGAGGGCAGGGTGGGTCGGGAA |
| 73 | c0515 | TGAGGGGAGGGAGGGAGGGAA |
| 74 | c0564 | TGAGGGGAGGGCGGGACGGGAA |
| 75 | c0199 | TGAGGGACGGGAGGGTGGGAA |
| 76 | c0579 | TGAGGGGTGGGAGGGAGGGAA |
| 77 | c0714 | TGAGGGGCGGGAGGGGTGGGAA |
| 78 | c0967 | TGAGGGCCGGGAGGGTGGGAA |
| 79 | c0727 | TGAGGGGCGGGTGGGTGGGAA |
| 80 | c0328 | TGAGGGTTGGGAGGGTCGGGAA |

TABLE 3

| SEQ ID NO: | Name | Sequence |
|---|---|---|
| 81 | c0499 | TGAGGGTCGGGCGGGAGGGAA |
| 82 | c0708 | TGAGGGGCGGGAGGGACGGGAA |
| 83 | c0608 | TGAGGGGTGGGTGGGCCGGGAA |
| 84 | c0535 | TGAGGGGAGGGTGGGTGGGAA |
| 85 | c0596 | TGAGGGGTGGGTGGGACGGGAA |
| 86 | e0024 | CTGGGTGGGTGGGCGGGA |
| 87 | c0160 | TGAGGGAGGGTGGGCCGGGAA |
| 88 | c0710 | TGAGGGGCGGGAGGGTTGGGAA |
| 89 | c0592 | TGAGGGGTGGGAGGGCCGGGAA |
| 90 | c0706 | TGAGGGGCGGGAGGGATGGGAA |
| 91 | c0528 | TGAGGGAGGGAGGGCCGGGAA |
| 92 | c0563 | TGAGGGGAGGGCGGGAGGGAA |
| 93 | c0723 | TGAGGGGCGGGTGGGAGGGAA |
| 94 | c0211 | TGAGGGACGGGTGGGAGGGAA |
| 95 | c0179 | TGAGGGAGGGCGGGAGGGAA |
| 96 | c0634 | TGAGGGGTGGGCGGGGTGGGAA |
| 97 | c0588 | TGAGGGGTGGGAGGGCGGGAA |
| 98 | c0467 | TGAGGGTCGGGTGGGAGGGAA |
| 99 | c0589 | TGAGGGGTGGGAGGGCAGGGAA |

TABLE 3-continued

| SEQ ID NO: | Name | Sequence |
|---|---|---|
| 100 | c0716 | TGAGGGGCGGGAGGGGCGGGAA |
| 101 | c0522 | TGAGGGGAGGGAGGGGTGGGAA |
| 102 | c0724 | TGAGGGGCGGGTGGGACGGGAA |
| 103 | c0516 | TGAGGGGAGGGAGGGACGGGAA |
| 104 | c0582 | TGAGGGGTGGGAGGGTTGGGAA |
| 105 | c0580 | TGAGGGGTGGGAGGGACGGGAA |
| 106 | c0581 | TGAGGGGTGGGAGGGTAGGGAA |
| 107 | c0590 | TGAGGGGTGGGAGGGCTGGGAA |
| 108 | c0527 | TGAGGGGAGGGAGGGCGGGAA |
| 109 | c0532 | TGAGGGGAGGGTGGGACGGGAA |
| 110 | e0013 | CTGGGAGGGCGGGAGGGA |
| 111 | e0052 | CTGGGCGGGAGGGCGGGA |
| 112 | c0730 | TGAGGGGCGGGTGGGGTGGGAA |
| 113 | c0521 | TGAGGGGAGGGAGGGGAGGGAA |
| 114 | e0050 | CTGGGCGGGAGGGTGGGA |
| 115 | c0540 | TGAGGGGAGGGTGGGGCGGGAA |
| 116 | c0915 | TGAGGGCGGGTGGGAGGGGAA |
| 117 | c0570 | TGAGGGGAGGGCGGGGTGGGAA |
| 118 | c0734 | TGAGGGGCGGGTGGGCTGGGAA |
| 119 | t1011 | GGGTGGGAAGGGAGG |
| 120 | c0764 | TGAGGGGCGGGCGGGGCGGGAA |

TABLE 4

| SEQ ID NO: | Name | Sequence |
|---|---|---|
| 123 | t1113 | GGGAGGGACGGGAGG |
| 124 | c0900 | TGAGGGCGGGGAGGGACGGGAA |
| 125 | c0899 | TGAGGGCGGGGAGGGAGGGGAA |
| 126 | c0766 | TGAGGGGCGGGCGGGCTGGGAA |
| 127 | c0573 | TGAGGGGAGGGCGGGCAGGGAA |
| 128 | t0420 | GGGCGGGAGGGAGGG |
| 129 | t1102 | GGGAGGAAGGGTGGG |
| 130 | c0602 | TGAGGGGTGGGTGGGGTGGGAA |
| 131 | c0585 | TGAGGGGTGGGAGGGGAGGGAA |
| 132 | c0536 | TGAGGGGAGGGTGGGTCGGGAA |

In the polynucleotide (b), "one or more" is not limited as long as the polynucleotide (b) is in a range of having redox activity, for example. The "one or more" is, for example, from 1 to 5, preferably from 1 to 3, more preferably from 1 or 2 in any of the base sequences in the polynucleotide (a).

In the polynucleotide (c), "an identity" is not limited as long as the polynucleotide (c) is in a range of having redox activity, for example. The identity is, for example, 80% or more, 85% or more, preferably 90% or more, more preferably 95% or more, 96% or more, 97% or more, yet more preferably 98% or more, particularly preferably 99% or more. The identity can be calculated by an analysis software program such as BLAST or FASTA using default parameters, for example (the same applies hereinafter).

In the polynucleotide (d), "a polynucleotide that can hybridize" is, for example, a polynucleotide completely or partially complementary to the polynucleotide (a). The hybridization can be detected by any of various hybridization assays, for example. The hybridization assays are not particularly limited, and for example, a method described in Sambrook et al., Molecular Cloning: A Laboratory Manual 2nd Ed., Cold Spring Harbor Laboratory Press (1989) or the like can be employed.

In the polynucleotide (d), the "stringent conditions" may be, for example, any of low stringent conditions, middle stringent conditions, and high stringent conditions. The "low stringent conditions" are, for example, conditions of 5×SSC, 5×Denhardt's solution, 0.5% SDS, 50% formamide, and 32° C. The "middle stringent conditions" are, for example, conditions of 5×SSC, 5×Denhardt's solution, 0.5% SDS, 50% formamide, and 42° C. The "high stringent conditions" are, for example, conditions of 5×SSC, 5×Denhardt's solution, 0.5% SDS, 50% formamide, and 50° C. Those skilled in the art can set the extent of stringency by appropriately selecting conditions such the temperature, the salt concentration, the concentration and the length of a probe, the ionic strength, and the time, for example. As the "stringent conditions", conditions described in Molecular Cloning: A Laboratory Manual 2nd Ed., Cold Spring Harbor Laboratory Press (1989) can be employed, for example.

A component of the polynucleotide is, for example, a nucleotide residue. Examples of the nucleic acid molecule according to the present invention include DNA composed of only a deoxyribonucleotide residue and DNA containing one or more ribonucleotide residues. In the latter case, the one or more is not particularly limited and is, for example, from 1 to 3, preferably 1 or 2 in the polynucleotide.

In the nucleic acid molecule according to the present invention, the polynucleotide is preferably a single-stranded polynucleotide. It is preferred that the single-stranded polynucleotide is capable of forming a stem structure and a loop structure by self-annealing, for example. It is preferred that the polynucleotide is capable of forming a stem-loop structure, an internal loop structure, and/or a bulge structure, for example.

The nucleic acid molecule according to the present invention may be, for example, a double-stranded polynucleotide. When the nucleic acid molecule according to the present invention is a double-stranded polynucleotide, one of single-stranded polynucleotides of the double-stranded polynucleotide is any of the above-described polynucleotides, and the other single-stranded polynucleotide is not limited, for example. The other single-stranded polynucleotide can be, for example, a polynucleotide composed of a base sequence complementary to any of the above-described polynucleotides. When the nucleic acid molecule according to the present invention is a double-stranded polynucleotide, it is preferred that the double-stranded polynucleotide is dissociated into single-stranded polynucleotides by denaturation or the like prior to the use thereof, for example. The dissociated single-stranded polynucleotides may form a stem structure and a loop structure as mentioned above, for example.

In the present invention, "being capable of forming a stem structure and a loop structure" includes: actually forming a stem structure and a loop structure; and being capable of forming a stem structure and a loop structure even if they are not formed, for example. "Bing capable of forming a stem structure and a loop structure" includes the case where the formation is checked experimentally and the case where the formation is predicted by a simulation using a computer or the like, for example.

The nucleic acid molecule according to the present invention has redox activity, so that it can be used as a substitute for oxidoreductase and is applicable to detection of a target using an aptamer such as mentioned above, for example.

EXAMPLES

Example 1

A. Consideration of Conditions

The conditions under which a redox reaction of a nucleic acid molecule to be evaluated was detected were considered.
(1) Immobilization of Polynucleotide A known polynucleotide was immobilized, via a spacer, on an electrode of a commercially available electrochemical detection-type microarray (trade name: CombiMatrix ElectraSense microarray, manufactured by CombiMatrix) as shown below.

In the known polynucleotide, EAD2 (SEQ ID NO: 133) (see Cheng, X., et al., (2009), Biochemistry, 48, 7817-7823) was used as DNAzyme. As a negative control, DNA aptamer SA (SEQ ID NO: 134) that binds to streptavidin was used.

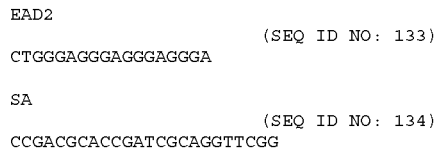

The lengths of the spacer were 0-mer (no spacer), 8-mer, 16-mer, and 24-mer. The sequence of the spacer was poly dT.

The immobilization was performed by binding the 3' end of the spacer with one electrode of the microarray and binding the 3' end of the known polynucleotide to the 5' end of the spacer. 250 each of four kinds of EAD2s (dT0, dT8, dT16, dT24) having different lengths of the spacer and four kinds of SAs (dT0, dT8, dT16, dT24) having different lengths of the spacer were randomly immobilized on the microarray.
(2) Detection of Redox Reaction Hydrogen peroxide was added to the microarray as a substrate, and an electrical signal generated by a redox reaction was measured as a current. In the measurement, a measurement device (product name: ElectraSense Reader, manufactured by CombiMatrix) was used (hereinafter the same). Hydrogen peroxide was added to various buffer solutions so as to have predetermined concentrations (0, 1, 2, 4, 8 mmol/L), and the resultant solutions were added as substrate solutions. As the buffer solutions, a tris buffer solution (pH7.4), a tris buffer solution (pH8.0), a tris buffer solution (pH8.5), and a tris buffer solution (pH9.0) were used, and the pHs of the resultant solutions were adjusted so as to have each pH in parentheses after the addition of hydrogen peroxide.

Figure 1B:
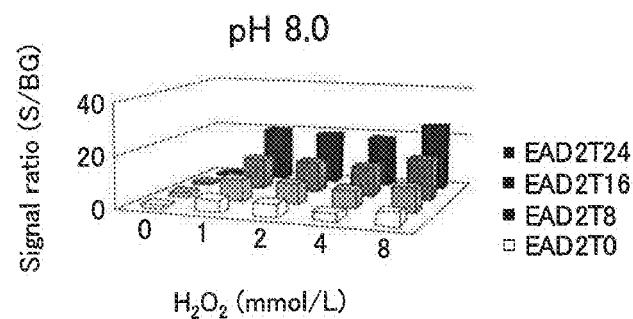
Figure 1C:
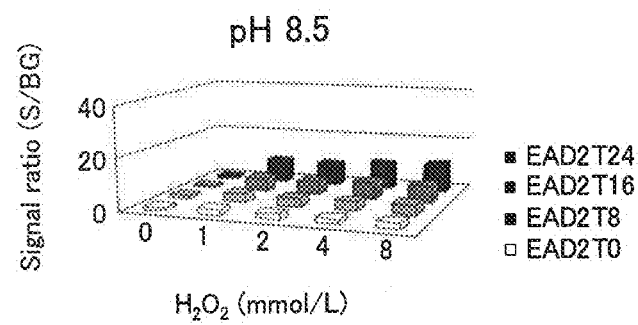
Figure 1D:
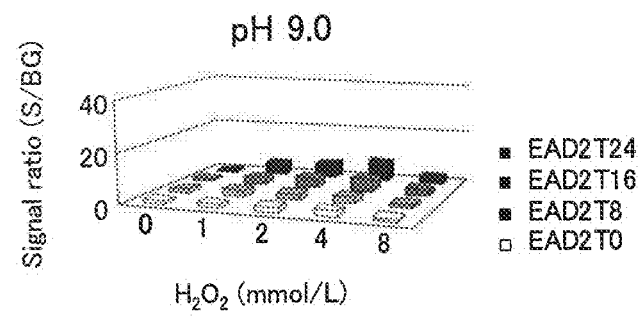

Results of these are shown in FIGS. 1A to 1D. FIGS. 1A to 1D are graphs showing electrical signals under each condition. FIG. 1A shows results in the case of pH7.4, FIG. 1B shows results in the case of pH8.0, FIG. 1C shows results in the case of pH8.5, and FIG. 1D shows results in the case of pH9.0. Each of FIGS. 1A to 1D shows results under different conditions of the concentration of hydrogen peroxide and the length of the spacer. In each of FIGS. 1A to 1D, the vertical axis indicates a signal ratio (S/BG) of the electrical signal (S) of EAD2 and the electrical signal (background: BG) of the negative control. As shown in FIG. 1A, the electrical signal reached maximum under the conditions of pH7.4, the concentration of hydrogen peroxide of 2 mmol/L, and the length of the spacer of 24-mer.

B. Reproducibility

Redox reactions of 250 each of four kinds of EAD2s (dT0, dT8, dT16, dT24) having different lengths of the spacer were measured under the same conditions as in "A. Consideration of conditions".

Figure 2A:
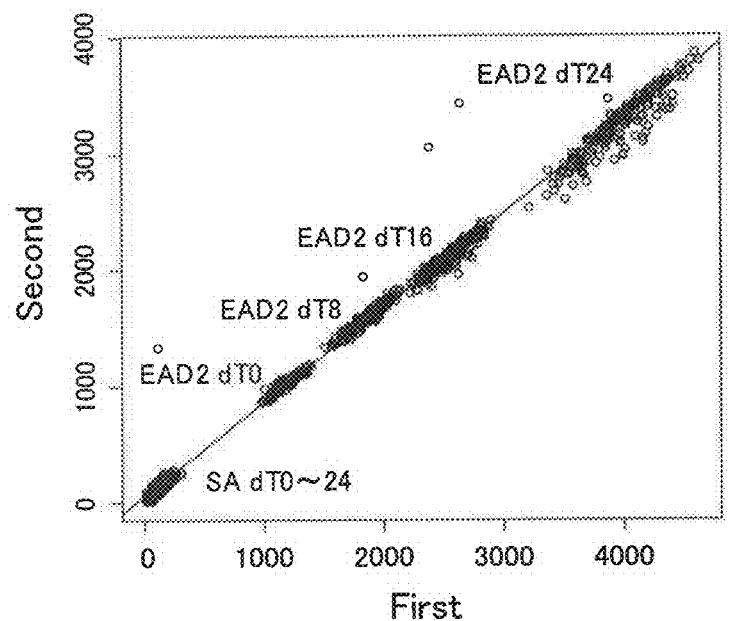
FIGS. 2A and 2B are graphs showing electrical signals of DNAzyme in Example 1 of the present invention.
Figure 2B:
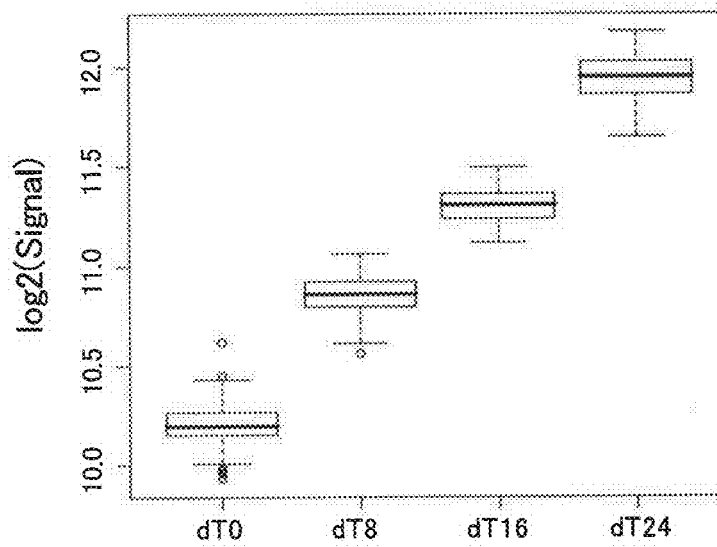

Results of these are shown in FIGS. 2A and 2B. FIG. 2A is a graph obtained by plotting first-time measurement values and second-time measurement values of the EAD2s and the SAs. The measurement values are signal measurement values that are obtained using the measurement device and correspond to currents. (hereinafter the same). The horizontal axis indicates the first-time signal measurement values, and the vertical axis indicates the second-time signal measurement values. FIG. 2B is a graph showing the logarithm of signal values of each EAD2 by the length of the spacer. The graph of FIG. 2A also shows a result of a test of no correlation of Pearson's correlation coefficient. In FIG. 2A, a correlation coefficient R=0.9981756. In FIG. 2B, the standard deviations of the respective lengths of the spacer were 0.09954021 in the case of dT0, 0.09435911 in the case of dT8, 0.08528754 in the case of dT16, and 0.1027817 in the case of dT24. As shown in FIGS. 2A and 2B, the results obtained by the measurements of 250 each of four kinds of EAD2s showed really high reproducibility.

C. Normality

Whether or not the results obtained by the measurements of 250 each of four kinds of EAD2s (dT0, dT8, dT16, dT24) having different lengths of the spacer and the results obtained by the measurements of 250 each of four kinds of SAs (dT0, dT8, dT16, dT24) having different lengths of the spacer in "A. Consideration of conditions" were normally-distributed was checked. In addition, a P value was determined by a Kolmoforov-Smirnov test.

Figure 3:
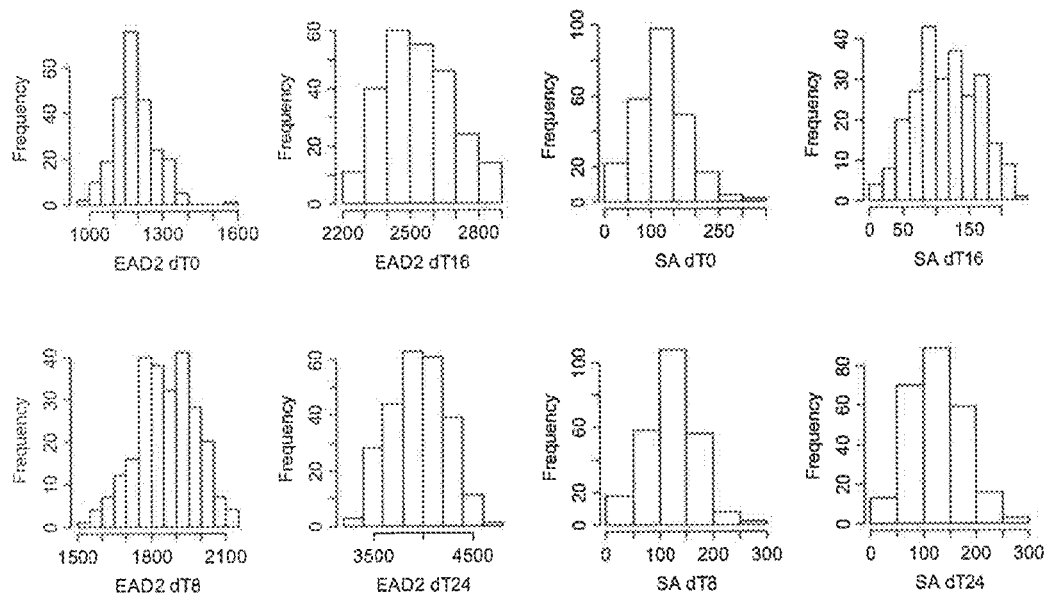
FIG. 3 shows graphs showing a relationship between an electrical signal value and its frequency with respect to each DNAzyme in Example 1 of the present invention.

Results of these are shown in FIG. 3. FIG. 3 shows graphs showing a relationship between a signal value and its frequency with respect to each EAD2 and each SA. It was determined that signals of 250 each of EAD2s and SAs were normally distributed as shown in FIG. 3.

Example 2

A plurality of polynucleotides composed of different sequences were immobilized on a microarray chip, and redox reactions thereof were measured.

A. Reproducibility

As shown below, a plurality of polynucleotides were immobilized, via a spacer composed of 24-mer poly dT, on an electrode of a commercially available microarray chip (trade name: CustomArray (registered trademark) 12K, manufactured by CombiMatrix).

In the polynucleotides, as DNAzyme, EAD2 (SEQ ID NO: 133), an aptamer SA (SEQ ID NO: 134), c-Myc (SEQ ID NO: 135) that is a partial sequence in a promoter region of a transcription factor c-Myc gene, and TA (SEQ ID NO: 136) that is an aptamer to thrombin were used.

EAD2
(SEQ ID NO: 133)
CTGGGAGGGAGGGAGGGA

SA
(SEQ ID NO: 134)
CCGACGCACCGATCGCAGGTTCGG c-Myc
(SEQ ID NO: 135)
TGAGGGTGGGGAGGGTGGGGAA

TA
(SEQ ID NO: 136)
GGTTGGTGTGGTTGG

Moreover, modified polynucleotides obtained by modifying sequences of the EAD2 (SEQ ID NO: 133), the c-Myc (SEQ ID NO: 135), and the TA (SEQ ID NO: 136) also were used in the same manner as described above. 64 kinds of modified EAD2 obtained by modifying the EAD2, 1024 kinds of modified c-Myc obtained by modifying the c-Myc, and 1232 kinds of modified TA obtained by modifying the TA were provided.

The immobilization was performed by binding the 3' end of the spacer with an electrode of one microarray and binding the 3' end of the known polynucleotide or the modified polynucleotide with the 5' end of the spacer. 100 each of the EAD2, the c-Myc, and the TA as controls of redox activity and 5 each of the modified polynucleotides were randomly immobilized on the microarray chip.

Then, redox reactions were measured three times under the same conditions using the same microarray chip. Specifically, a tris buffer solution (pH7.4) containing 2 mmol/L hydrogen peroxide was added to the microarray chip, and electrical signals generated by the redox reactions were measured as currents.

Figure 4A:
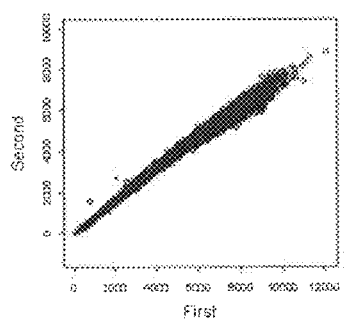
FIGS. 4A to 4C are graphs showing electrical signals of DNAzyme in Example 2 of the present invention.
Figure 4B:
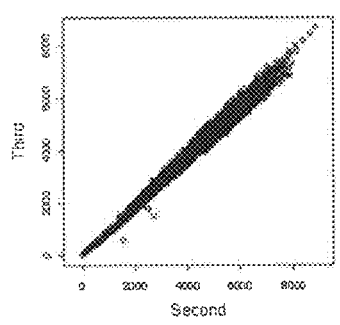
Figure 4C:
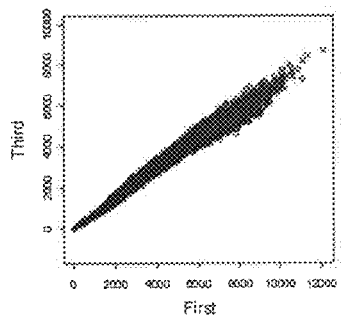

Results of these are shown in FIGS. 4A to 4C. In FIGS. 4A to 4C, FIG. 4A is a graph obtained by plotting first-time measurement values and second-time measurement values. FIG. 4B is a graph obtained by plotting the second-time measurement values and third-time measurement values. FIG. 4C is a graph obtained by plotting the first-time measurement values and the third-time measurement values. Each of the graphs also shows a result of a test of no correlation of Pearson's correlation coefficient. As shown in FIGS. 4A to 4C, the results showed really high reproducibility in the same array.

B. Normality

Figure 5A:
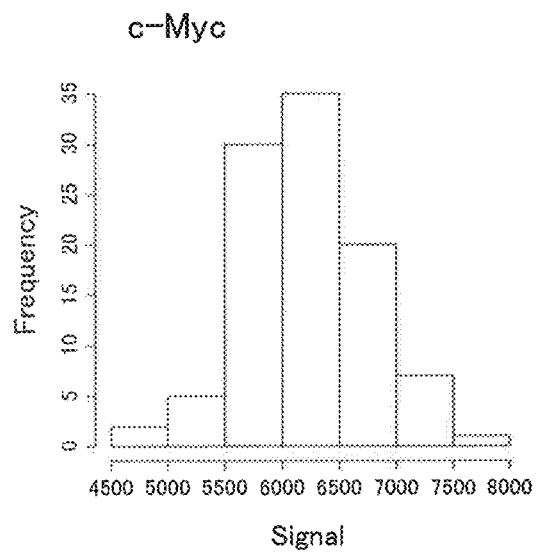
FIGS. 5A to 5D are graphs showing a relationship between an electrical signal value and its frequency of each DNAzyme in Example 2 of the present invention.
Figure 5B:
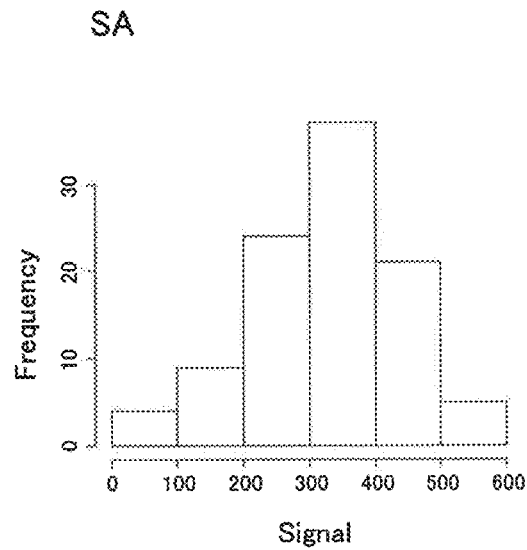
Figure 5C:
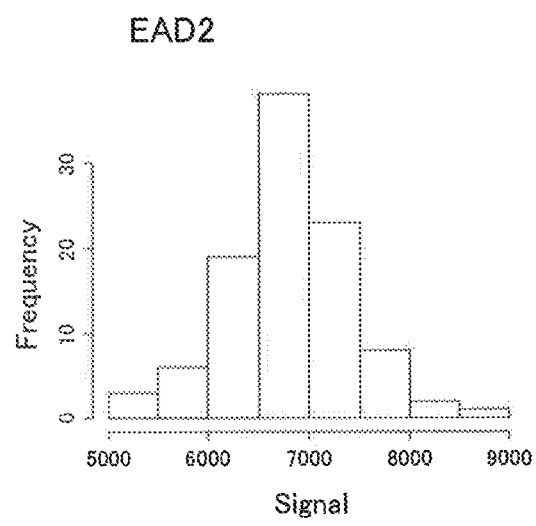
Figure 5D:
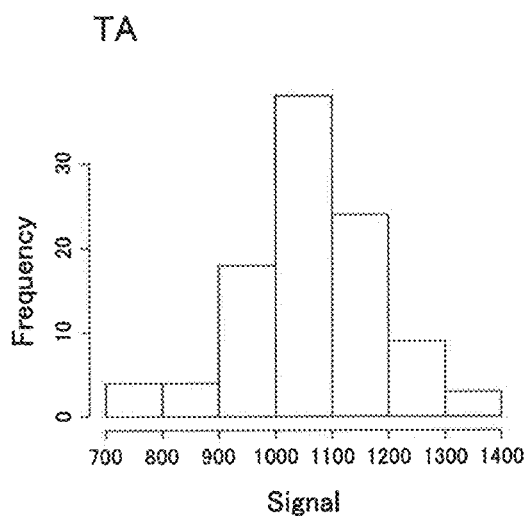

In graphs of FIGS. 5A to 5D, based on the results obtained by the measurement in "A. Reproducibility", FIG. 5A shows a relationship between a signal value and its frequency of 100 c-Mycs, FIG. 5B shows a relationship between a signal value and its frequency of 100 SAs, FIG. 5C shows a relationship between a signal value and its frequency of 100 EAD2s, and FIG. 5D shows a relationship between a signal value and its frequency of 100 TAs. It was determined that the signals were normally distributed in each of the graphs.

Example 3

New DNAzyme having high redox activity was screened using the microarray chip of Example 2.

Figure 6:
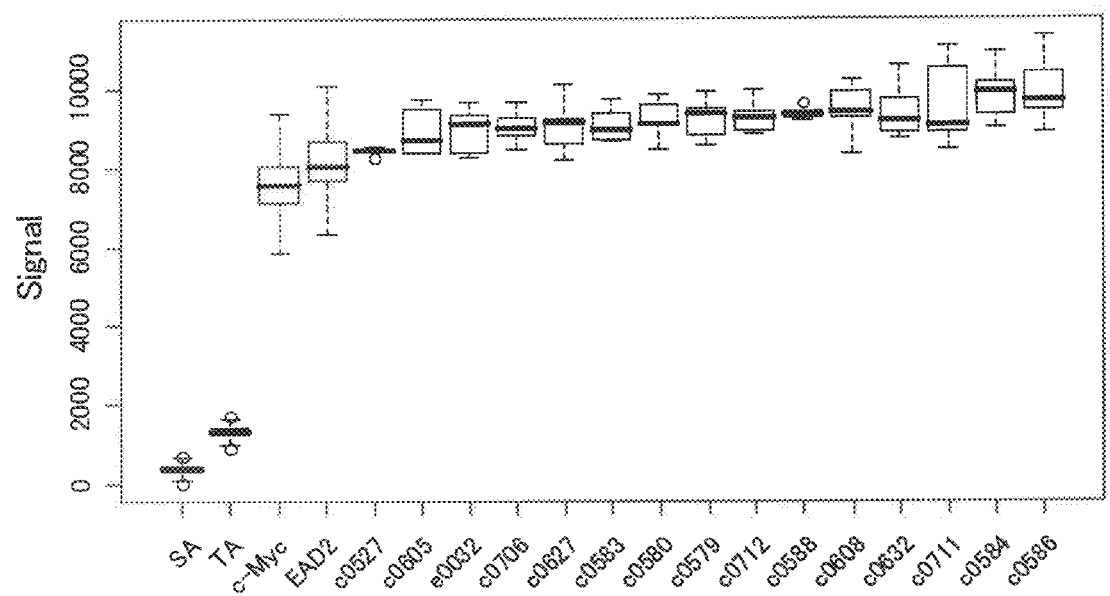
FIG. 6 is a graph showing an electrical signal value of each DNAzyme in Example 3 of the present invention.

From the result obtained by the three-time measurements in Example 2, a modified polynucleotide exerting high activity compared with EAD2 was found. This result is shown in FIG. 6. FIG. 6 is a graph showing signal values of SA, EAD2, c-Myc, and TA as controls of redox activity and 15 kinds of modified polynucleotides exerting redox activity. As shown in FIG. 6, these modified polynucleotides showed high redox activity compared with EAD2. It was determined by a T test that the signal values of these 15 kinds of modified polynucleotides were significant to EAD2. The sequences of these 15 kinds of modified polynucleotides are shown below.

TABLE 5

| SEQ ID NO: | Name  | Sequence                 |
|------------|-------|--------------------------|
| 15         | c0711 | TGAGGGGCGGGAGGGTGGGGAA   |
| 22         | c0712 | TGAGGGGCGGGAGGGTCGGGAA   |
| 30         | e0032 | CTGGGTGGGCGGGCGGGA       |
| 33         | c0605 | TGAGGGGTGGGTGGGCAGGGAA   |
| 35         | c0586 | TGAGGGGTGGGAGGGGTGGGAA   |
| 39         | c0632 | TGAGGGGTGGGCGGGTCGGGAA   |
| 50         | c0584 | TGAGGGGTGGGAGGGTCGGGAA   |
| 55         | c0627 | TGAGGGGTGGGCGGGAGGGGAA   |
| 65         | c0583 | TGAGGGGTGGGAGGGTGGGGAA   |
| 76         | c0579 | TGAGGGGTGGGAGGGAGGGGAA   |
| 83         | c0608 | TGAGGGGTGGGTGGGCCGGGAA   |
| 90         | c0706 | TGAGGGGCGGGAGGGATGGGAA   |
| 97         | c0588 | TGAGGGGTGGGAGGGCGGGAA    |
| 105        | c0580 | TGAGGGGTGGGAGGGACGGGAA   |
| 108        | c0537 | TGAGGGGAGGGAGGGCGGGGAA   |

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims This application is based upon and claims the benefit of priority from Japanese patent application No. 2011-448562, filed on Jul. 4, 2011, the disclosure of which is incorporated herein its entirety by reference.

INDUSTRIAL APPLICABILITY

According to the present invention, the presence or absence or the intensity of redox activity of a nucleic acid molecule to be evaluated can be evaluated easily. Moreover, by such evaluation method according to the present invention, a plurality of nucleic acid molecules can be evaluated at the same time. Thus, an intended nucleic acid molecule can be screened efficiently, for example. As mentioned above, for example, the nucleic acid molecule having redox activity can be used as a substitute for an enzyme such as peroxidase and is thus useful in various fields such as clinical medical care, food, and environment.

The invention claimed is:

1. A method for evaluating redox activity of a nucleic acid molecule, the method comprising:
   a detection step of electrochemically detecting a redox reaction to a substrate using a device that electrochemically detects a redox reaction, wherein the redox reaction is catalyzed by at least one nucleic acid molecule to be evaluated; and
   an evaluation step of evaluating redox activity of the at least one nucleic acid molecule from a result of the detection of the redox reaction, wherein
   the device includes a base provided with a detection portion,
   the detection portion includes an electrode system, and
   the nucleic acid molecule to be evaluated is arranged, via a linker of polynucleotide having a length of from 20 to 30 bases, on the base.

2. The method according to claim 1, wherein the at least one nucleic acid molecule to be evaluated comprises a plurality of kinds of nucleic acid molecules.

3. The method according to claim 2, wherein the base is a microarray in which the plurality of kinds of nucleic acid molecules is arranged.

4. The method according to any one of claims 1 to 3, wherein the detection step is a step of detecting a redox reaction catalyzed by the nucleic acid molecule in the presence of the substrate.

5. The method according to any one of claims 1 to 3, wherein a nucleic acid aptamer capable of binding to a target is bound to the nucleic acid molecule to be evaluated.

6. The method according to claim 5, wherein the detection step is a step of detecting a redox reaction catalyzed by the nucleic acid molecule in the presence of the substrate and the target.

7. The method according to claim 5, wherein the detection step comprises:
   a step of detecting the redox reaction in the presence of the substrate and in the absence of the target; and
   a step of detecting the redox reaction in the presence of the substrate and the target, and
   in the evaluation step evaluating the redox activity, in the presence of the target, of a nucleic acid molecule that does not exert the redox activity in the absence of the target.

8. A method for screening a nucleic acid molecule having redox activity, the method comprising:
   evaluating redox activity of at least one nucleic acid molecule to be evaluated by the method according to any one of claims 1 to 3 using a device; and
   screening a nucleic acid molecule having redox activity.

9. The method according to claim 4, wherein a nucleic acid aptamer capable of binding to a target is bound to the nucleic acid molecule to be evaluated.

10. The method according to claim 9, wherein the detection step is a step of detecting a redox reaction catalyzed by the nucleic acid molecule in the presence of the substrate and the target.

11. The method according to claim 9, wherein
   the detection step comprises:
   a step of detecting the redox reaction in the presence of the substrate and in the absence of the target; and
   a step of detecting the redox reaction in the presence of the substrate and the target, and
   in the evaluation step, the redox activity in the presence of the target, of a nucleic acid molecule that does not exert the redox activity in the absence of the target is evaluated.

12. The method according to claim 6, wherein the detection step comprises:
   a step of detecting the redox reaction in the presence of the substrate and in the absence of the target; and
   a step of detecting the redox reaction in the presence of the substrate and the target, and
   in the evaluation step, the redox activity in the presence of the target, of a nucleic acid molecule that does not exert the redox activity in the absence of the target is evaluated.

13. The method according to claim 10, wherein the detection step comprises:
   a step of detecting the redox reaction in the presence of the substrate and in the absence of the target; and
   a step of detecting the redox reaction in the presence of the substrate and the target, and
   in the evaluation step, the redox activity in the presence of the target, of a nucleic acid molecule that does not exert the redox activity in the absence of the target is evaluated.

14. A method for screening a nucleic acid molecule having redox activity, the method comprising:
   evaluating redox activity of at least one nucleic acid molecule to be evaluated by the method according to claim 4 using a device; and
   screening a nucleic acid molecule having redox activity.

15. A method for screening a nucleic acid molecule having redox activity, the method comprising:
   evaluating redox activity of at least one nucleic acid molecule to be evaluated by the method according to claim 5 using a device; and
   screening a nucleic acid molecule having redox activity.

16. A method for screening a nucleic acid molecule having redox activity, the method comprising:
   evaluating redox activity of at least one nucleic acid molecule to be evaluated by the method according to claim 9 using a device; and
   screening a nucleic acid molecule having redox activity.

17. A method for screening a nucleic acid molecule having redox activity, the method comprising:
   evaluating redox activity of at least one nucleic acid molecule to be evaluated by the method according to claim 6 using a device; and
   screening a nucleic acid molecule having redox activity.

18. A method for screening a nucleic acid molecule having redox activity, the method comprising:
   evaluating redox activity of at least one nucleic acid molecule to be evaluated by the method according to claim 10 using a device; and
   screening a nucleic acid molecule having redox activity.

19. A method for screening a nucleic acid molecule having redox activity, the method comprising:
   evaluating redox activity of at least one nucleic acid molecule to be evaluated by the method according to claim 7 using a device; and
   screening a nucleic acid molecule having redox activity.

20. A method for screening a nucleic acid molecule having redox activity, the method comprising:
   evaluating redox activity of at least one nucleic acid molecule to be evaluated by the method according to claim 11 using a device; and
   screening a nucleic acid molecule having redox activity.

21. A method for screening a nucleic acid molecule having redox activity, the method comprising:
   evaluating redox activity of at least one nucleic acid molecule to be evaluated by the method according to claim 12 using a device; and screening a nucleic acid molecule having redox activity.

22. A method for screening a nucleic acid molecule having redox activity, the method comprising:
- evaluating redox activity of at least one nucleic acid molecule to be evaluated by the method according to claim 13 using a device; and
- screening a nucleic acid molecule having redox activity.

* * * * *

SEQUENCE LISTING

<160> NUMBER OF SEQ ID NOS: 136

<210> SEQ ID NO 1
<211> LENGTH: 22
<212> TYPE: DNA
<213> ORGANISM: Artificial Sequence
<220> FEATURE:
<223> OTHER INFORMATION: DNAzyme

<400> SEQUENCE: 1
tgagggccgg gtgggtcggg aa    22

<210> SEQ ID NO 2
<211> LENGTH: 22
<212> TYPE: DNA
<213> ORGANISM: Artificial Sequence
<220> FEATURE:
<223> OTHER INFORMATION: DNAzyme

<400> SEQUENCE: 2 tgagggggagg gcgggtcggg aa    22

<210> SEQ ID NO 3
<211> LENGTH: 22
<212> TYPE: DNA
<213> ORGANISM: Artificial Sequence
<220> FEATURE:
<223> OTHER INFORMATION: DNAzyme

<400> SEQUENCE: 3
tgagggatgg gagggagggg aa    22

<210> SEQ ID NO 4
<211> LENGTH: 22
<212> TYPE: DNA
<213> ORGANISM: Artificial Sequence
<220> FEATURE:
<223> OTHER INFORMATION: DNAzyme

<400> SEQUENCE: 4
tgagggaggg gcgggccggg aa    22

<210> SEQ ID NO 5
<211> LENGTH: 22
<212> TYPE: DNA
<213> ORGANISM: Artificial Sequence
<220> FEATURE:
<223> OTHER INFORMATION: DNAzyme

<400> SEQUENCE: 5
tgaggggagg gaggggcggg aa    22

<210> SEQ ID NO 6
<211> LENGTH: 22
<212> TYPE: DNA
<213> ORGANISM: Artificial Sequence
<220> FEATURE:
<223> OTHER INFORMATION: DNAzyme

<400> SEQUENCE: 6
tgagggtcgg gagggagggg aa    22

<210> SEQ ID NO 7
<211> LENGTH: 22
<212> TYPE: DNA
<213> ORGANISM: Artificial Sequence

```
<220> FEATURE:
<223> OTHER INFORMATION: DNAzyme

<400> SEQUENCE: 7
tgaggggagg gtgggcaggg aa                                               22

<210> SEQ ID NO 8
<211> LENGTH: 22
<212> TYPE: DNA
<213> ORGANISM: Artificial Sequence
<220> FEATURE:
<223> OTHER INFORMATION: DNAzyme

<400> SEQUENCE: 8 tgagggtgg gcgggtaggg aa                                                22

<210> SEQ ID NO 9
<211> LENGTH: 22
<212> TYPE: DNA
<213> ORGANISM: Artificial Sequence
<220> FEATURE:
<223> OTHER INFORMATION: DNAzyme

<400> SEQUENCE: 9
tgagggaggg gcgggtcggg aa                                               22

<210> SEQ ID NO 10
<211> LENGTH: 22
<212> TYPE: DNA
<213> ORGANISM: Artificial Sequence
<220> FEATURE:
<223> OTHER INFORMATION: DNAzyme

<400> SEQUENCE: 10 tgagggcgg gcgggtcggg aa                                                22

<210> SEQ ID NO 11
<211> LENGTH: 22
<212> TYPE: DNA
<213> ORGANISM: Artificial Sequence
<220> FEATURE:
<223> OTHER INFORMATION: DNAzyme

<400> SEQUENCE: 11
tgaggggcgg gtgggtcggg aa                                               22

<210> SEQ ID NO 12
<211> LENGTH: 18
<212> TYPE: DNA
<213> ORGANISM: Artificial Sequence
<220> FEATURE:
<223> OTHER INFORMATION: DNAzyme

<400> SEQUENCE: 12
ctgggcgggc gggcggga                                                    18

<210> SEQ ID NO 13
<211> LENGTH: 22
<212> TYPE: DNA
<213> ORGANISM: Artificial Sequence
<220> FEATURE:
<223> OTHER INFORMATION: DNAzyme

<400> SEQUENCE: 13
tgaggggcgg gagggcgggg aa                                               22
```

```
<210> SEQ ID NO 14
<211> LENGTH: 22
<212> TYPE: DNA
<213> ORGANISM: Artificial Sequence
<220> FEATURE:
<223> OTHER INFORMATION: DNAzyme

<400> SEQUENCE: 14
tgaggggagg gtgggagggg aa                                              22

<210> SEQ ID NO 15
<211> LENGTH: 22
<212> TYPE: DNA
<213> ORGANISM: Artificial Sequence
<220> FEATURE:
<223> OTHER INFORMATION: DNAzyme

<400> SEQUENCE: 15
tgaggggcgg gagggtgggg aa                                              22

<210> SEQ ID NO 16
<211> LENGTH: 22
<212> TYPE: DNA
<213> ORGANISM: Artificial Sequence
<220> FEATURE:
<223> OTHER INFORMATION: DNAzyme

<400> SEQUENCE: 16
tgagggatgg gtgggccggg aa                                              22

<210> SEQ ID NO 17
<211> LENGTH: 22
<212> TYPE: DNA
<213> ORGANISM: Artificial Sequence
<220> FEATURE:
<223> OTHER INFORMATION: DNAzyme

<400> SEQUENCE: 17 tgagggtgg gtgggagggg aa                                               22

<210> SEQ ID NO 18
<211> LENGTH: 22
<212> TYPE: DNA
<213> ORGANISM: Artificial Sequence
<220> FEATURE:
<223> OTHER INFORMATION: DNAzyme

<400> SEQUENCE: 18
tgagggttgg gagggcgggg aa                                              22

<210> SEQ ID NO 19
<211> LENGTH: 22
<212> TYPE: DNA
<213> ORGANISM: Artificial Sequence
<220> FEATURE:
<223> OTHER INFORMATION: DNAzyme

<400> SEQUENCE: 19
tgagggtcgg gagggtcggg aa                                              22

<210> SEQ ID NO 20
<211> LENGTH: 22
<212> TYPE: DNA
<213> ORGANISM: Artificial Sequence
<220> FEATURE:
<223> OTHER INFORMATION: DNAzyme
```

```
<400> SEQUENCE: 20
tgaggggcgg gcgggacggg aa                                          22

<210> SEQ ID NO 21
<211> LENGTH: 22
<212> TYPE: DNA
<213> ORGANISM: Artificial Sequence
<220> FEATURE:
<223> OTHER INFORMATION: DNAzyme

<400> SEQUENCE: 21
tgaggggcgg gagggcaggg aa                                          22

<210> SEQ ID NO 22
<211> LENGTH: 22
<212> TYPE: DNA
<213> ORGANISM: Artificial Sequence
<220> FEATURE:
<223> OTHER INFORMATION: DNAzyme

<400> SEQUENCE: 22
tgaggggcgg gagggtcggg aa                                          22

<210> SEQ ID NO 23
<211> LENGTH: 22
<212> TYPE: DNA
<213> ORGANISM: Artificial Sequence
<220> FEATURE:
<223> OTHER INFORMATION: DNAzyme

<400> SEQUENCE: 23 tgagggga gg gcgggatggg aa                                         22

<210> SEQ ID NO 24
<211> LENGTH: 22
<212> TYPE: DNA
<213> ORGANISM: Artificial Sequence
<220> FEATURE:
<223> OTHER INFORMATION: DNAzyme

<400> SEQUENCE: 24
tgaggggcgg gagggga ggg aa                                         22

<210> SEQ ID NO 25
<211> LENGTH: 22
<212> TYPE: DNA
<213> ORGANISM: Artificial Sequence
<220> FEATURE:
<223> OTHER INFORMATION: DNAzyme

<400> SEQUENCE: 25
tgaggggcgg gtgggcgggg aa                                          22

<210> SEQ ID NO 26
<211> LENGTH: 18
<212> TYPE: DNA
<213> ORGANISM: Artificial Sequence
<220> FEATURE:
<223> OTHER INFORMATION: DNAzyme

<400> SEQUENCE: 26
ctgggtgggt gggaggga                                               18
```

```
<210> SEQ ID NO 27
<211> LENGTH: 22
<212> TYPE: DNA
<213> ORGANISM: Artificial Sequence
<220> FEATURE:
<223> OTHER INFORMATION: DNAzyme

<400> SEQUENCE: 27
tgaggggtgg gtgggcgggg aa                                              22

<210> SEQ ID NO 28
<211> LENGTH: 22
<212> TYPE: DNA
<213> ORGANISM: Artificial Sequence
<220> FEATURE:
<223> OTHER INFORMATION: DNAzyme

<400> SEQUENCE: 28 tgagggcgg gtgggatggg aa                                               22

<210> SEQ ID NO 29
<211> LENGTH: 22
<212> TYPE: DNA
<213> ORGANISM: Artificial Sequence
<220> FEATURE:
<223> OTHER INFORMATION: DNAzyme

<400> SEQUENCE: 29
tgaggggtgg gtgggtcggg aa                                              22

<210> SEQ ID NO 30
<211> LENGTH: 18
<212> TYPE: DNA
<213> ORGANISM: Artificial Sequence
<220> FEATURE:
<223> OTHER INFORMATION: DNAzyme

<400> SEQUENCE: 30
ctgggtgggc gggcggga                                                   18

<210> SEQ ID NO 31
<211> LENGTH: 22
<212> TYPE: DNA
<213> ORGANISM: Artificial Sequence
<220> FEATURE:
<223> OTHER INFORMATION: DNAzyme

<400> SEQUENCE: 31
tgaggggagg gtgggccggg aa                                              22

<210> SEQ ID NO 32
<211> LENGTH: 22
<212> TYPE: DNA
<213> ORGANISM: Artificial Sequence
<220> FEATURE:
<223> OTHER INFORMATION: DNAzyme

<400> SEQUENCE: 32
tgagggtcgg gagggtgggg aa                                              22

<210> SEQ ID NO 33
<211> LENGTH: 22
<212> TYPE: DNA
<213> ORGANISM: Artificial Sequence
<220> FEATURE:
<223> OTHER INFORMATION: DNAzyme
```

```
<400> SEQUENCE: 33
tgaggggtgg gtgggcaggg aa                                                22

<210> SEQ ID NO 34
<211> LENGTH: 22
<212> TYPE: DNA
<213> ORGANISM: Artificial Sequence
<220> FEATURE:
<223> OTHER INFORMATION: DNAzyme

<400> SEQUENCE: 34
tgaggggcgg gagggctggg aa                                                22

<210> SEQ ID NO 35
<211> LENGTH: 22
<212> TYPE: DNA
<213> ORGANISM: Artificial Sequence
<220> FEATURE:
<223> OTHER INFORMATION: DNAzyme

<400> SEQUENCE: 35
tgaggggtgg gagggtggg aa                                                 22

<210> SEQ ID NO 36
<211> LENGTH: 22
<212> TYPE: DNA
<213> ORGANISM: Artificial Sequence
<220> FEATURE:
<223> OTHER INFORMATION: DNAzyme

<400> SEQUENCE: 36
tgagggttgg gtgggtcggg aa                                                22

<210> SEQ ID NO 37
<211> LENGTH: 22
<212> TYPE: DNA
<213> ORGANISM: Artificial Sequence
<220> FEATURE:
<223> OTHER INFORMATION: DNAzyme

<400> SEQUENCE: 37
tgagggaggg gtgggtcggg aa                                                22

<210> SEQ ID NO 38
<211> LENGTH: 22
<212> TYPE: DNA
<213> ORGANISM: Artificial Sequence
<220> FEATURE:
<223> OTHER INFORMATION: DNAzyme

<400> SEQUENCE: 38
tgaggggtgg gcgggttggg aa                                                22

<210> SEQ ID NO 39
<211> LENGTH: 22
<212> TYPE: DNA
<213> ORGANISM: Artificial Sequence
<220> FEATURE:
<223> OTHER INFORMATION: DNAzyme

<400> SEQUENCE: 39
tgaggggtgg gcgggtcggg aa                                                22
```

```
<210> SEQ ID NO 40
<211> LENGTH: 22
<212> TYPE: DNA
<213> ORGANISM: Artificial Sequence
<220> FEATURE:
<223> OTHER INFORMATION: DNAzyme

<400> SEQUENCE: 40
tgaggggtgg gcgggatggg aa                                              22

<210> SEQ ID NO 41
<211> LENGTH: 22
<212> TYPE: DNA
<213> ORGANISM: Artificial Sequence
<220> FEATURE:
<223> OTHER INFORMATION: DNAzyme

<400> SEQUENCE: 41
tgaggggcgg gcggggtggg aa                                              22

<210> SEQ ID NO 42
<211> LENGTH: 22
<212> TYPE: DNA
<213> ORGANISM: Artificial Sequence
<220> FEATURE:
<223> OTHER INFORMATION: DNAzyme

<400> SEQUENCE: 42
tgaggggcgg gagggagggg aa                                              22

<210> SEQ ID NO 43
<211> LENGTH: 22
<212> TYPE: DNA
<213> ORGANISM: Artificial Sequence
<220> FEATURE:
<223> OTHER INFORMATION: DNAzyme

<400> SEQUENCE: 43
tgaggggcgg gcgggtgggg aa                                              22

<210> SEQ ID NO 44
<211> LENGTH: 22
<212> TYPE: DNA
<213> ORGANISM: Artificial Sequence
<220> FEATURE:
<223> OTHER INFORMATION: DNAzyme

<400> SEQUENCE: 44
tgaggggagg gtgggcgggg aa                                              22

<210> SEQ ID NO 45
<211> LENGTH: 22
<212> TYPE: DNA
<213> ORGANISM: Artificial Sequence
<220> FEATURE:
<223> OTHER INFORMATION: DNAzyme

<400> SEQUENCE: 45
tgaggggtgg gcgggcaggg aa                                              22

<210> SEQ ID NO 46
<211> LENGTH: 22
<212> TYPE: DNA
<213> ORGANISM: Artificial Sequence
<220> FEATURE:
<223> OTHER INFORMATION: DNAzyme
```

```
<400> SEQUENCE: 46
tgaggggtgg gtgggctggg aa                                              22

<210> SEQ ID NO 47
<211> LENGTH: 22
<212> TYPE: DNA
<213> ORGANISM: Artificial Sequence
<220> FEATURE:
<223> OTHER INFORMATION: DNAzyme

<400> SEQUENCE: 47
tgagggctgg gcgggcgggg aa                                              22

<210> SEQ ID NO 48
<211> LENGTH: 22
<212> TYPE: DNA
<213> ORGANISM: Artificial Sequence
<220> FEATURE:
<223> OTHER INFORMATION: DNAzyme

<400> SEQUENCE: 48
tgaggggcgg gcgggaaggg aa                                              22

<210> SEQ ID NO 49
<211> LENGTH: 22
<212> TYPE: DNA
<213> ORGANISM: Artificial Sequence
<220> FEATURE:
<223> OTHER INFORMATION: DNAzyme

<400> SEQUENCE: 49
tgaggggtgg gcgggaaggg aa                                              22

<210> SEQ ID NO 50
<211> LENGTH: 22
<212> TYPE: DNA
<213> ORGANISM: Artificial Sequence
<220> FEATURE:
<223> OTHER INFORMATION: DNAzyme

<400> SEQUENCE: 50
tgaggggtgg gagggtcggg aa                                              22

<210> SEQ ID NO 51
<211> LENGTH: 22
<212> TYPE: DNA
<213> ORGANISM: Artificial Sequence
<220> FEATURE:
<223> OTHER INFORMATION: DNAzyme

<400> SEQUENCE: 51
tgaggggagg gcgggtgggg aa                                              22

<210> SEQ ID NO 52
<211> LENGTH: 22
<212> TYPE: DNA
<213> ORGANISM: Artificial Sequence
<220> FEATURE:
<223> OTHER INFORMATION: DNAzyme

<400> SEQUENCE: 52
tgaggggtgg gtgggtgggg aa                                              22
```

<210> SEQ ID NO 53
<211> LENGTH: 22
<212> TYPE: DNA
<213> ORGANISM: Artificial Sequence
<220> FEATURE:
<223> OTHER INFORMATION: DNAzyme

<400> SEQUENCE: 53
tgaggggagg gagggtcggg aa                                              22

<210> SEQ ID NO 54
<211> LENGTH: 22
<212> TYPE: DNA
<213> ORGANISM: Artificial Sequence
<220> FEATURE:
<223> OTHER INFORMATION: DNAzyme

<400> SEQUENCE: 54
tgaggggtgg gcggggcggg aa                                              22

<210> SEQ ID NO 55
<211> LENGTH: 22
<212> TYPE: DNA
<213> ORGANISM: Artificial Sequence
<220> FEATURE:
<223> OTHER INFORMATION: DNAzyme

<400> SEQUENCE: 55
tgaggggtgg gcgggagggg aa                                              22

<210> SEQ ID NO 56
<211> LENGTH: 22
<212> TYPE: DNA
<213> ORGANISM: Artificial Sequence
<220> FEATURE:
<223> OTHER INFORMATION: DNAzyme

<400> SEQUENCE: 56
tgaggggagg gagggtgggg aa                                              22

<210> SEQ ID NO 57
<211> LENGTH: 22
<212> TYPE: DNA
<213> ORGANISM: Artificial Sequence
<220> FEATURE:
<223> OTHER INFORMATION: DNAzyme

<400> SEQUENCE: 57
tgagggttgg gtgggtgggg aa                                              22

<210> SEQ ID NO 58
<211> LENGTH: 22
<212> TYPE: DNA
<213> ORGANISM: Artificial Sequence
<220> FEATURE:
<223> OTHER INFORMATION: DNAzyme

<400> SEQUENCE: 58
tgaggggtgg gcgggacggg aa                                              22

<210> SEQ ID NO 59
<211> LENGTH: 22
<212> TYPE: DNA
<213> ORGANISM: Artificial Sequence
<220> FEATURE:
<223> OTHER INFORMATION: DNAzyme

```
<400> SEQUENCE: 59
tgagggttgg gcgggcgggg aa                                              22

<210> SEQ ID NO 60
<211> LENGTH: 22
<212> TYPE: DNA
<213> ORGANISM: Artificial Sequence
<220> FEATURE:
<223> OTHER INFORMATION: DNAzyme

<400> SEQUENCE: 60
tgagggctgg gtgggtcggg aa                                              22

<210> SEQ ID NO 61
<211> LENGTH: 22
<212> TYPE: DNA
<213> ORGANISM: Artificial Sequence
<220> FEATURE:
<223> OTHER INFORMATION: DNAzyme

<400> SEQUENCE: 61
tgaggggcgg gagggtaggg aa                                              22

<210> SEQ ID NO 62
<211> LENGTH: 22
<212> TYPE: DNA
<213> ORGANISM: Artificial Sequence
<220> FEATURE:
<223> OTHER INFORMATION: DNAzyme

<400> SEQUENCE: 62
tgaggggagg gcgggctggg aa                                              22

<210> SEQ ID NO 63
<211> LENGTH: 22
<212> TYPE: DNA
<213> ORGANISM: Artificial Sequence
<220> FEATURE:
<223> OTHER INFORMATION: DNAzyme

<400> SEQUENCE: 63
tgagggctgg gaggggtggg aa                                              22

<210> SEQ ID NO 64
<211> LENGTH: 22
<212> TYPE: DNA
<213> ORGANISM: Artificial Sequence
<220> FEATURE:
<223> OTHER INFORMATION: DNAzyme

<400> SEQUENCE: 64
tgaggggtgg gcgggctggg aa                                              22

<210> SEQ ID NO 65
<211> LENGTH: 22
<212> TYPE: DNA
<213> ORGANISM: Artificial Sequence
<220> FEATURE:
<223> OTHER INFORMATION: DNAzyme

<400> SEQUENCE: 65
tgaggggtgg gagggtgggg aa                                              22
```

```
<210> SEQ ID NO 66
<211> LENGTH: 22
<212> TYPE: DNA
<213> ORGANISM: Artificial Sequence
<220> FEATURE:
<223> OTHER INFORMATION: DNAzyme

<400> SEQUENCE: 66
tgagggtcgg gtgggtcggg aa                                              22

<210> SEQ ID NO 67
<211> LENGTH: 22
<212> TYPE: DNA
<213> ORGANISM: Artificial Sequence
<220> FEATURE:
<223> OTHER INFORMATION: DNAzyme

<400> SEQUENCE: 67
tgagggtcgg gagggcgggg aa                                              22

<210> SEQ ID NO 68
<211> LENGTH: 18
<212> TYPE: DNA
<213> ORGANISM: Artificial Sequence
<220> FEATURE:
<223> OTHER INFORMATION: DNAzyme

<400> SEQUENCE: 68
ctgggtggga gggtggga                                                   18

<210> SEQ ID NO 69
<211> LENGTH: 22
<212> TYPE: DNA
<213> ORGANISM: Artificial Sequence
<220> FEATURE:
<223> OTHER INFORMATION: DNAzyme

<400> SEQUENCE: 69
tgaggggcgg gtgggccggg aa                                              22

<210> SEQ ID NO 70
<211> LENGTH: 22
<212> TYPE: DNA
<213> ORGANISM: Artificial Sequence
<220> FEATURE:
<223> OTHER INFORMATION: DNAzyme

<400> SEQUENCE: 70 tgagggtgg gtggggcggg aa                                               22

<210> SEQ ID NO 71
<211> LENGTH: 22
<212> TYPE: DNA
<213> ORGANISM: Artificial Sequence
<220> FEATURE:
<223> OTHER INFORMATION: DNAzyme

<400> SEQUENCE: 71 tgagggtgg gagggcgggg aa                                               22

<210> SEQ ID NO 72
<211> LENGTH: 22
<212> TYPE: DNA
<213> ORGANISM: Artificial Sequence
<220> FEATURE:
<223> OTHER INFORMATION: DNAzyme
```

```
<400> SEQUENCE: 72
tgagggcagg gtgggtcggg aa                                              22

<210> SEQ ID NO 73
<211> LENGTH: 22
<212> TYPE: DNA
<213> ORGANISM: Artificial Sequence
<220> FEATURE:
<223> OTHER INFORMATION: DNAzyme

<400> SEQUENCE: 73
tgaggggagg gagggagggg aa                                              22

<210> SEQ ID NO 74
<211> LENGTH: 22
<212> TYPE: DNA
<213> ORGANISM: Artificial Sequence
<220> FEATURE:
<223> OTHER INFORMATION: DNAzyme

<400> SEQUENCE: 74
tgaggggagg gcgggacggg aa                                              22

<210> SEQ ID NO 75
<211> LENGTH: 22
<212> TYPE: DNA
<213> ORGANISM: Artificial Sequence
<220> FEATURE:
<223> OTHER INFORMATION: DNAzyme

<400> SEQUENCE: 75
tgagggacgg gagggtgggg aa                                              22

<210> SEQ ID NO 76
<211> LENGTH: 22
<212> TYPE: DNA
<213> ORGANISM: Artificial Sequence
<220> FEATURE:
<223> OTHER INFORMATION: DNAzyme

<400> SEQUENCE: 76
tgaggggtgg gagggagggg aa                                              22

<210> SEQ ID NO 77
<211> LENGTH: 22
<212> TYPE: DNA
<213> ORGANISM: Artificial Sequence
<220> FEATURE:
<223> OTHER INFORMATION: DNAzyme

<400> SEQUENCE: 77
tgaggggcgg gaggggtggg aa                                              22

<210> SEQ ID NO 78
<211> LENGTH: 22
<212> TYPE: DNA
<213> ORGANISM: Artificial Sequence
<220> FEATURE:
<223> OTHER INFORMATION: DNAzyme

<400> SEQUENCE: 78
tgagggccgg gagggtgggg aa                                              22
```

```
<210> SEQ ID NO 79
<211> LENGTH: 22
<212> TYPE: DNA
<213> ORGANISM: Artificial Sequence
<220> FEATURE:
<223> OTHER INFORMATION: DNAzyme

<400> SEQUENCE: 79
tgaggggcgg gtgggtgggg aa                                              22

<210> SEQ ID NO 80
<211> LENGTH: 22
<212> TYPE: DNA
<213> ORGANISM: Artificial Sequence
<220> FEATURE:
<223> OTHER INFORMATION: DNAzyme

<400> SEQUENCE: 80
tgagggttgg gagggtcggg aa                                              22

<210> SEQ ID NO 81
<211> LENGTH: 22
<212> TYPE: DNA
<213> ORGANISM: Artificial Sequence
<220> FEATURE:
<223> OTHER INFORMATION: DNAzyme

<400> SEQUENCE: 81
tgagggtcgg gcgggagggg aa                                              22

<210> SEQ ID NO 82
<211> LENGTH: 22
<212> TYPE: DNA
<213> ORGANISM: Artificial Sequence
<220> FEATURE:
<223> OTHER INFORMATION: DNAzyme

<400> SEQUENCE: 82 tgagggggcgg gagggacggg aa                                             22

<210> SEQ ID NO 83
<211> LENGTH: 22
<212> TYPE: DNA
<213> ORGANISM: Artificial Sequence
<220> FEATURE:
<223> OTHER INFORMATION: DNAzyme

<400> SEQUENCE: 83
tgaggggtgg gtgggccggg aa                                              22

<210> SEQ ID NO 84
<211> LENGTH: 22
<212> TYPE: DNA
<213> ORGANISM: Artificial Sequence
<220> FEATURE:
<223> OTHER INFORMATION: DNAzyme

<400> SEQUENCE: 84
tgaggggagg gtgggtgggg aa                                              22

<210> SEQ ID NO 85
<211> LENGTH: 22
<212> TYPE: DNA
<213> ORGANISM: Artificial Sequence
<220> FEATURE:
<223> OTHER INFORMATION: DNAzyme
```

```
<400> SEQUENCE: 85
tgaggggtgg gtgggacggg aa                                    22

<210> SEQ ID NO 86
<211> LENGTH: 18
<212> TYPE: DNA
<213> ORGANISM: Artificial Sequence
<220> FEATURE:
<223> OTHER INFORMATION: DNAzyme

<400> SEQUENCE: 86
ctgggtgggt gggcggga                                         18

<210> SEQ ID NO 87
<211> LENGTH: 22
<212> TYPE: DNA
<213> ORGANISM: Artificial Sequence
<220> FEATURE:
<223> OTHER INFORMATION: DNAzyme

<400> SEQUENCE: 87
tgagggaggg gtgggccggg aa                                    22

<210> SEQ ID NO 88
<211> LENGTH: 22
<212> TYPE: DNA
<213> ORGANISM: Artificial Sequence
<220> FEATURE:
<223> OTHER INFORMATION: DNAzyme

<400> SEQUENCE: 88
tgaggggcgg gagggttggg aa                                    22

<210> SEQ ID NO 89
<211> LENGTH: 22
<212> TYPE: DNA
<213> ORGANISM: Artificial Sequence
<220> FEATURE:
<223> OTHER INFORMATION: DNAzyme

<400> SEQUENCE: 89
tgaggggtgg gagggccggg aa                                    22

<210> SEQ ID NO 90
<211> LENGTH: 22
<212> TYPE: DNA
<213> ORGANISM: Artificial Sequence
<220> FEATURE:
<223> OTHER INFORMATION: DNAzyme

<400> SEQUENCE: 90
tgaggggcgg gagggatggg aa                                    22

<210> SEQ ID NO 91
<211> LENGTH: 22
<212> TYPE: DNA
<213> ORGANISM: Artificial Sequence
<220> FEATURE:
<223> OTHER INFORMATION: DNAzyme

<400> SEQUENCE: 91
tgaggggagg gagggccggg aa                                    22
```

```
<210> SEQ ID NO 92
<211> LENGTH: 22
<212> TYPE: DNA
<213> ORGANISM: Artificial Sequence
<220> FEATURE:
<223> OTHER INFORMATION: DNAzyme

<400> SEQUENCE: 92
tgaggggagg gcgggagggg aa                                              22

<210> SEQ ID NO 93
<211> LENGTH: 22
<212> TYPE: DNA
<213> ORGANISM: Artificial Sequence
<220> FEATURE:
<223> OTHER INFORMATION: DNAzyme

<400> SEQUENCE: 93
tgaggggcgg gtgggagggg aa                                              22

<210> SEQ ID NO 94
<211> LENGTH: 22
<212> TYPE: DNA
<213> ORGANISM: Artificial Sequence
<220> FEATURE:
<223> OTHER INFORMATION: DNAzyme

<400> SEQUENCE: 94
tgagggacgg gtgggagggg aa                                              22

<210> SEQ ID NO 95
<211> LENGTH: 22
<212> TYPE: DNA
<213> ORGANISM: Artificial Sequence
<220> FEATURE:
<223> OTHER INFORMATION: DNAzyme

<400> SEQUENCE: 95
tgagggaggg gcgggagggg aa                                              22

<210> SEQ ID NO 96
<211> LENGTH: 22
<212> TYPE: DNA
<213> ORGANISM: Artificial Sequence
<220> FEATURE:
<223> OTHER INFORMATION: DNAzyme

<400> SEQUENCE: 96
tgaggggtgg gcggggtggg aa                                              22

<210> SEQ ID NO 97
<211> LENGTH: 22
<212> TYPE: DNA
<213> ORGANISM: Artificial Sequence
<220> FEATURE:
<223> OTHER INFORMATION: DNAzyme

<400> SEQUENCE: 97
tgaggggtgg gaggggcggg aa                                              22

<210> SEQ ID NO 98
<211> LENGTH: 22
<212> TYPE: DNA
<213> ORGANISM: Artificial Sequence
<220> FEATURE:
<223> OTHER INFORMATION: DNAzyme
```

```
<400> SEQUENCE: 98
tgagggtcgg gtgggagggg aa                                          22

<210> SEQ ID NO 99
<211> LENGTH: 22
<212> TYPE: DNA
<213> ORGANISM: Artificial Sequence
<220> FEATURE:
<223> OTHER INFORMATION: DNAzyme

<400> SEQUENCE: 99 tgagggtgg gagggcaggg aa                                           22

<210> SEQ ID NO 100
<211> LENGTH: 22
<212> TYPE: DNA
<213> ORGANISM: Artificial Sequence
<220> FEATURE:
<223> OTHER INFORMATION: DNAzyme

<400> SEQUENCE: 100
tgaggggcgg gaggggcggg aa                                          22

<210> SEQ ID NO 101
<211> LENGTH: 22
<212> TYPE: DNA
<213> ORGANISM: Artificial Sequence
<220> FEATURE:
<223> OTHER INFORMATION: DNAzyme

<400> SEQUENCE: 101
tgaggggagg gaggggtggg aa                                          22

<210> SEQ ID NO 102
<211> LENGTH: 22
<212> TYPE: DNA
<213> ORGANISM: Artificial Sequence
<220> FEATURE:
<223> OTHER INFORMATION: DNAzyme

<400> SEQUENCE: 102
tgaggggcgg gtgggacggg aa                                          22

<210> SEQ ID NO 103
<211> LENGTH: 22
<212> TYPE: DNA
<213> ORGANISM: Artificial Sequence
<220> FEATURE:
<223> OTHER INFORMATION: DNAzyme

<400> SEQUENCE: 103
tgaggggagg gagggacggg aa                                          22

<210> SEQ ID NO 104
<211> LENGTH: 22
<212> TYPE: DNA
<213> ORGANISM: Artificial Sequence
<220> FEATURE:
<223> OTHER INFORMATION: DNAzyme

<400> SEQUENCE: 104 tgagggtgg gagggttggg aa                                           22
```

```
<210> SEQ ID NO 105
<211> LENGTH: 22
<212> TYPE: DNA
<213> ORGANISM: Artificial Sequence
<220> FEATURE:
<223> OTHER INFORMATION: DNAzyme

<400> SEQUENCE: 105
tgaggggtgg gagggacggg aa                                             22

<210> SEQ ID NO 106
<211> LENGTH: 22
<212> TYPE: DNA
<213> ORGANISM: Artificial Sequence
<220> FEATURE:
<223> OTHER INFORMATION: DNAzyme

<400> SEQUENCE: 106
tgaggggtgg gagggtaggg aa                                             22

<210> SEQ ID NO 107
<211> LENGTH: 22
<212> TYPE: DNA
<213> ORGANISM: Artificial Sequence
<220> FEATURE:
<223> OTHER INFORMATION: DNAzyme

<400> SEQUENCE: 107
tgaggggtgg gagggctggg aa                                             22

<210> SEQ ID NO 108
<211> LENGTH: 22
<212> TYPE: DNA
<213> ORGANISM: Artificial Sequence
<220> FEATURE:
<223> OTHER INFORMATION: DNAzyme

<400> SEQUENCE: 108
tgaggggagg gagggcgggg aa                                             22

<210> SEQ ID NO 109
<211> LENGTH: 22
<212> TYPE: DNA
<213> ORGANISM: Artificial Sequence
<220> FEATURE:
<223> OTHER INFORMATION: DNAzyme

<400> SEQUENCE: 109
tgaggggagg gtgggacggg aa                                             22

<210> SEQ ID NO 110
<211> LENGTH: 18
<212> TYPE: DNA
<213> ORGANISM: Artificial Sequence
<220> FEATURE:
<223> OTHER INFORMATION: DNAzyme

<400> SEQUENCE: 110
ctgggagggc gggaggga                                                  18

<210> SEQ ID NO 111
<211> LENGTH: 18
<212> TYPE: DNA
<213> ORGANISM: Artificial Sequence
<220> FEATURE:
<223> OTHER INFORMATION: DNAzyme
```

```
<400> SEQUENCE: 111
ctgggcggga gggcggga                                                    18

<210> SEQ ID NO 112
<211> LENGTH: 22
<212> TYPE: DNA
<213> ORGANISM: Artificial Sequence
<220> FEATURE:
<223> OTHER INFORMATION: DNAzyme

<400> SEQUENCE: 112
tgaggggcgg gtggggtggg aa                                               22

<210> SEQ ID NO 113
<211> LENGTH: 22
<212> TYPE: DNA
<213> ORGANISM: Artificial Sequence
<220> FEATURE:
<223> OTHER INFORMATION: DNAzyme

<400> SEQUENCE: 113 tgagggga gg gaggggaggg aa                                              22

<210> SEQ ID NO 114
<211> LENGTH: 18
<212> TYPE: DNA
<213> ORGANISM: Artificial Sequence
<220> FEATURE:
<223> OTHER INFORMATION: DNAzyme

<400> SEQUENCE: 114
ctgggcggga gggtggga                                                    18

<210> SEQ ID NO 115
<211> LENGTH: 22
<212> TYPE: DNA
<213> ORGANISM: Artificial Sequence
<220> FEATURE:
<223> OTHER INFORMATION: DNAzyme

<400> SEQUENCE: 115
tgaggggagg gtggggcggg aa                                               22

<210> SEQ ID NO 116
<211> LENGTH: 22
<212> TYPE: DNA
<213> ORGANISM: Artificial Sequence
<220> FEATURE:
<223> OTHER INFORMATION: DNAzyme

<400> SEQUENCE: 116
tgagggcggg gtgggagggg aa                                               22

<210> SEQ ID NO 117
<211> LENGTH: 22
<212> TYPE: DNA
<213> ORGANISM: Artificial Sequence
<220> FEATURE:
<223> OTHER INFORMATION: DNAzyme

<400> SEQUENCE: 117
tgaggggagg gcggggtggg aa                                               22
```

```
<210> SEQ ID NO 118
<211> LENGTH: 22
<212> TYPE: DNA
<213> ORGANISM: Artificial Sequence
<220> FEATURE:
<223> OTHER INFORMATION: DNAzyme

<400> SEQUENCE: 118
tgaggggcgg gtgggctggg aa                                              22

<210> SEQ ID NO 119
<211> LENGTH: 15
<212> TYPE: DNA
<213> ORGANISM: Artificial Sequence
<220> FEATURE:
<223> OTHER INFORMATION: DNAzyme

<400> SEQUENCE: 119
gggtgggaag ggagg                                                      15

<210> SEQ ID NO 120
<211> LENGTH: 22
<212> TYPE: DNA
<213> ORGANISM: Artificial Sequence
<220> FEATURE:
<223> OTHER INFORMATION: DNAzyme

<400> SEQUENCE: 120
tgaggggcgg gcggggcggg aa                                              22

<210> SEQ ID NO 121
<211> LENGTH: 22
<212> TYPE: DNA
<213> ORGANISM: Artificial Sequence
<220> FEATURE:
<223> OTHER INFORMATION: DNAzyme

<400> SEQUENCE: 121
tgaggggcgg gtggggcggg aa                                              22

<210> SEQ ID NO 122
<211> LENGTH: 22
<212> TYPE: DNA
<213> ORGANISM: Artificial Sequence
<220> FEATURE:
<223> OTHER INFORMATION: DNAzyme

<400> SEQUENCE: 122
tgagggaggg gcgggcaggg aa                                              22

<210> SEQ ID NO 123
<211> LENGTH: 15
<212> TYPE: DNA
<213> ORGANISM: Artificial Sequence
<220> FEATURE:
<223> OTHER INFORMATION: DNAzyme

<400> SEQUENCE: 123
gggagggacg ggagg                                                      15

<210> SEQ ID NO 124
<211> LENGTH: 22
<212> TYPE: DNA
<213> ORGANISM: Artificial Sequence
<220> FEATURE:
<223> OTHER INFORMATION: DNAzyme
```

```
<400> SEQUENCE: 124
tgagggcggg gagggacggg aa                                              22

<210> SEQ ID NO 125
<211> LENGTH: 22
<212> TYPE: DNA
<213> ORGANISM: Artificial Sequence
<220> FEATURE:
<223> OTHER INFORMATION: DNAzyme

<400> SEQUENCE: 125
tgagggcggg gagggagggg aa                                              22

<210> SEQ ID NO 126
<211> LENGTH: 22
<212> TYPE: DNA
<213> ORGANISM: Artificial Sequence
<220> FEATURE:
<223> OTHER INFORMATION: DNAzyme

<400> SEQUENCE: 126
tgaggggcgg gcgggctggg aa                                              22

<210> SEQ ID NO 127
<211> LENGTH: 22
<212> TYPE: DNA
<213> ORGANISM: Artificial Sequence
<220> FEATURE:
<223> OTHER INFORMATION: DNAzyme

<400> SEQUENCE: 127
tgaggggagg gcgggcaggg aa                                              22

<210> SEQ ID NO 128
<211> LENGTH: 15
<212> TYPE: DNA
<213> ORGANISM: Artificial Sequence
<220> FEATURE:
<223> OTHER INFORMATION: DNAzyme

<400> SEQUENCE: 128
gggcgggagg gaggg                                                      15

<210> SEQ ID NO 129
<211> LENGTH: 15
<212> TYPE: DNA
<213> ORGANISM: Artificial Sequence
<220> FEATURE:
<223> OTHER INFORMATION: DNAzyme

<400> SEQUENCE: 129
gggaggaagg gtggg                                                      15

<210> SEQ ID NO 130
<211> LENGTH: 22
<212> TYPE: DNA
<213> ORGANISM: Artificial Sequence
<220> FEATURE:
<223> OTHER INFORMATION: DNAzyme

<400> SEQUENCE: 130
tgaggggtgg gtgggtggg aa                                               22
```

```
<210> SEQ ID NO 131
<211> LENGTH: 22
<212> TYPE: DNA
<213> ORGANISM: Artificial Sequence
<220> FEATURE:
<223> OTHER INFORMATION: DNAzyme

<400> SEQUENCE: 131 tgagggggtgg gaggggaggg aa                                              22

<210> SEQ ID NO 132
<211> LENGTH: 22
<212> TYPE: DNA
<213> ORGANISM: Artificial Sequence
<220> FEATURE:
<223> OTHER INFORMATION: DNAzyme

<400> SEQUENCE: 132
tgaggggagg gtgggtcggg aa                                               22

<210> SEQ ID NO 133
<211> LENGTH: 18
<212> TYPE: DNA
<213> ORGANISM: Artificial Sequence
<220> FEATURE:
<223> OTHER INFORMATION: DNAzyme

<400> SEQUENCE: 133
ctgggaggga gggaggga                                                    18

<210> SEQ ID NO 134
<211> LENGTH: 24
<212> TYPE: DNA
<213> ORGANISM: Artificial Sequence
<220> FEATURE:
<223> OTHER INFORMATION: DNA aptamer

<400> SEQUENCE: 134
ccgacgcacc gatcgcaggt tcgg                                             24

<210> SEQ ID NO 135
<211> LENGTH: 22
<212> TYPE: DNA
<213> ORGANISM: Artificial Sequence
<220> FEATURE:
<223> OTHER INFORMATION: promoter

<400> SEQUENCE: 135
tgagggtggg gagggtgggg aa                                               22

<210> SEQ ID NO 136
<211> LENGTH: 15
<212> TYPE: DNA
<213> ORGANISM: Artificial Sequence
<220> FEATURE:
<223> OTHER INFORMATION: aptamer

<400> SEQUENCE: 136
ggttggtgtg gttgg                                                       15
```